US006207831B1

(12) United States Patent
Auer et al.

(10) Patent No.: US 6,207,831 B1
(45) Date of Patent: Mar. 27, 2001

(54) FLUORESCENT DYES (AIDA) FOR SOLID PHASE AND SOLUTION PHASE SCREENING

(75) Inventors: Manfred Auer, Moedling; Hubert Gstach, Vienna, both of (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/217,795

(22) Filed: Dec. 21, 1998

(51) Int. Cl.[7] ............... C07D 403/10; C07D 231/56; C07F 7/02
(52) U.S. Cl. ............... 544/371; 544/229; 548/110; 548/361.1
(58) Field of Search ............... 548/361.1, 110; 544/371, 229

(56) References Cited

U.S. PATENT DOCUMENTS 5,006,520   4/1991   Oe et al. .

FOREIGN PATENT DOCUMENTS 641564        3/1995   (EP) .
WO 98/41866   9/1998   (WO) .

OTHER PUBLICATIONS

Leandro Baiocchi et al., Indazoles and Dihydrophthalizines from N–Phenylhydrazidoyl Chlorides, J. Heterocyclic Chem., 20, 225, 1982.*
Gladstone et al., J. Chem. Soc. C 1966, 1781–1784.
Dennler et al., Tetrahedron, vol. 22, 3131–41, 1966.
Khomenko et al., Kinetika i Kataliz, vol. 7, No. 4, 671–8, 1966 (Chem. Abstr. 65:18454a (2 pp)).
Borsche, W. et al., "Zur Kenntnis der Benzisoxazole. II," Justus Liebigs Ann. Chem., vol. 540, 1939, pp. 83–98.
Chen, R.F., "Measurements of Absolute Values in Biochemical Fluorescence Spectroscopy," J. of Research of the International Bureau of Standards, vol. 76A, No. 6, 1972, pp. 593–606.
Dalla Croce, P. et al., A Convenient Synthesis of Indazoles, Synthesis, vol. 11, 1984, pp. 982–983.
Demas, J.N. et al., "The Measurement of Photoluminescence Quantum Yields. A Review," J. Phys. Chem., vol. 75, 1971, pp. 991–1024.
Dennler, E.B. et al., "Synthesis of Indazoles Using Polyphosphoric Acid—I," Tetrahedron, 1966, vol. 22, pp. 3131–3141.
Elderfield, R.C., "Heterocyclic Compounds," 1957, ed. Elderfield, R.C., vol. 5, John Wiley & Sons, Inc., New York, p. 162.
Fries, K. et al., "Untersuchungen in der Reihe des Indazols," Justus Liebigs Ann. Chem., vol. 454, 1927 pp. 303–324.
Fries, K. et al., "Untersuchungen in der Reihe des Indazols," Justus Liebigs Ann. Chem, vol. 550, 1941 pp. 31–49.
Gladstone, W.A.F. et al., "Reactions of Lead Tetra–acetate. Part II. A New Synthesis of 1–Arylindazoles," R.O.C.J. Chem. Soc., 1965, pp. 3048–3052.

Gladstone, W.A.F. et al., "Reactions of Lead Tetra–acetate. Part III. The Synthesis of 3–Alkyl–1–arylindazoles," J. Chem. Soc., 1965, pp. 5177–5182.
Gladstone, W.A.F. et al., "Reactions of Lead Tetra–acetate. Part VIII. The Reactions of Azoacetates with Base," J. Chem. Soc., 1966, p. 1781.
Huisgen, R. et al., "Diphenyl–Nitrilimin Und Seine 1.3–Dipolaren Additionen An Alkene Und Alkine," Tetrahedron, vol. 17, 1962, pp. 3–29.
Huisgen, R. et al., "Zur Anlagerung des Diphenylnitrilimins an nichtkonjugierte Alkene und Alkine; Sterischer Ablauf, Orientierung und Substituenteneinfluss," vol. 100, 1967, pp. 1580–1592.
Krishnan, R. et al., "Reactions of Hydroxybenzophenone with Hydrazines," Heterocycl. Chem., vol. 25, No. 2, 1988, pp. 447–45.
Lakowicz, J.R., Principles of Fluorescence Spectroscopy, Plenum Press, New York and London, 1983, pp. 52–93, pp. 112–153, pp. 156–185.
Matsugo, S. et al., "A New and Convenient Synthesis of 1H–Indazoles," Synthesis, 1983, p. 852.
Matsugo, S. et al., "Studies on 2,5–Diaryl–2,4–dihydro–3H–pyrazol–3–ones. I. Synthesis of Highly Substituted 1H–Indazoles Using Tautomeric 2,5–Diaryl–2,4–dihydro–3H–pyrazol–3–ones," Chem. Pharm. Bull, vol. 32, 1984, pp. 2146–2153.
Melhuish, W.H., "Quantum Efficiencies of Fluorescence of Organic Substances: Effect of Solvent and Concentration of the Fluorescent Solute," J. Phys. Chem., vol. 65, 1961, pp. 229–235.
Mishra, A.K. et al., "Some Effects of Phosphate Buffers on the Excited State Prototropic Equilibria of Indazole," J. Photochem., 1984, vol. 26, pp. 49–56.
Petrich, J.W. et al., "On the Origin of Nonexponential Fluorescence Decay in Tryptophan and Its Derivatives," J. Am. Chem. Soc., vol. 105, 1983, pp. 3824–3832.

(List continued on next page.)

Primary Examiner—Deborah C. Lambkin
Assistant Examiner—Sonya Wright
(74) Attorney, Agent, or Firm—Gabriel Lopez

(57) ABSTRACT

The invention relates to new fluorescent dyes of formula (I)

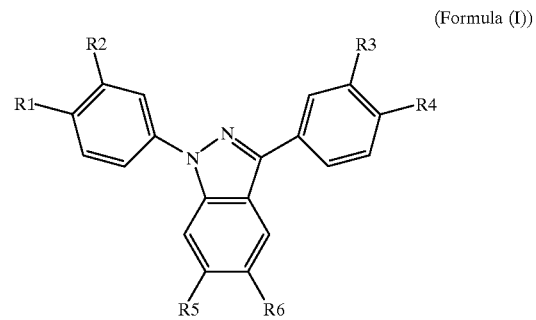

(Formula (I))

Figure 1:
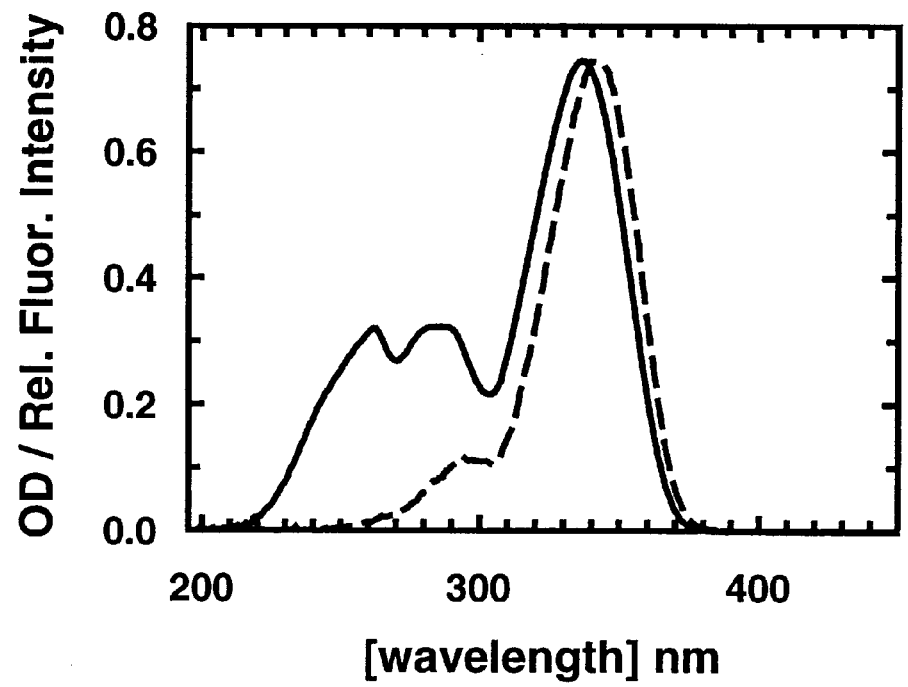
Figure 1:
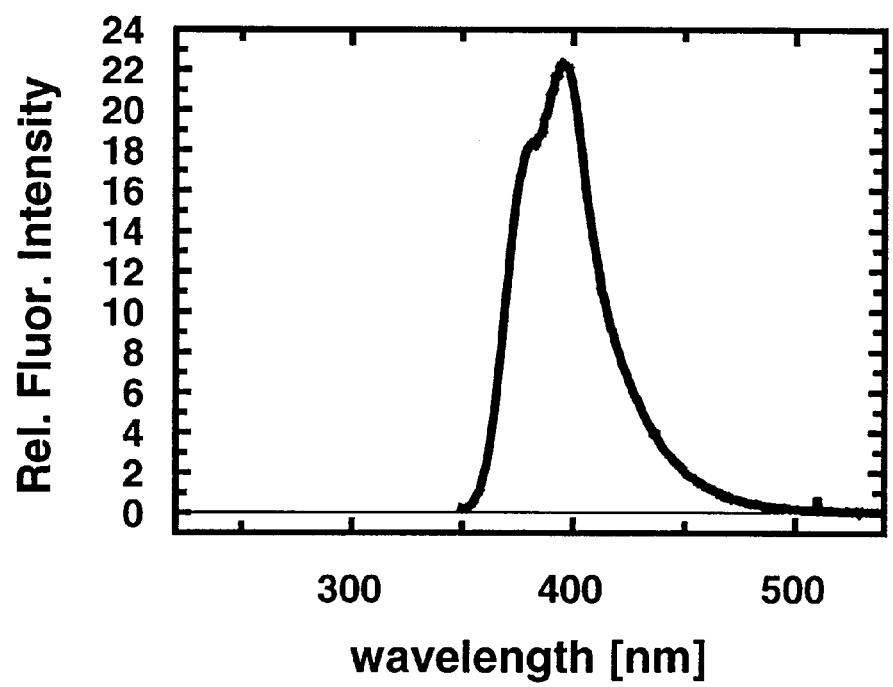

which can be used in high throughput screening both, on the solid phase as well as in homogeneous solution.

3 Claims, 4 Drawing Sheets

OTHER PUBLICATIONS

Phaniraj, P. et al., "Absorption & Fluorescence Spectra of 7–Aminoindazole: Study of Solvent & pH Dependences," Indian J. Chem., 1985, vol. 24A,, pp. 913–917.

Pugliese, L. et al., "Three–dimensional Structure of the Tetragonal Crystal Form of Egg–white Avidin in its functional Complex with Biotin at 2.7 A Resolution," J. Mol. Biol., vol. 231, 1993, pp. 698–710.

Pummerer, R. et al., "Über Diaroylhydrochinone, III. Mitteilung," Chem. Ber., vol. 84, 1951, pp. 583–590.

Saha, Subit K. et al., "Solvatochromic Effects in the Absorption and Fluorescence Spectra of Indazole and Its Amino Derivatives," J. Photochem. Photobiol, A, 1977, vol. 110, pp. 257–266.

Savage, M.D. et al., Avidin–Biotin Chemistry, Pierce Chemical Company, 1992.

Szabo, A.G. et al., "Fluorescence Decay of Tryptophan Conformers in Aqueous Solution," J. Am. Chem. Soc., vol. 105, 1983, pp. 3824–3832.

Theilacker, W. et al., "Synthese von 1–Arylindazolen," Tetrahedron Letters, No. 1, 1966, pp. 91–92.

Wang, Q. et al., "1,2,4–Triazolium Salts from the Reaction of 1–Aza–2–azoniaallene Salts with Nitriles," Synthesis, vol. 7, 1992, pp. 710–718.

Yan, B. et al., "An Indazole Synthesis on Solid support Monitored by Single Bead FTIR Microspectroscopy," Tetrahedron Letters, vol. 37, No. 46, pp. 8325–8328, 1996.

\* cited by examiner

FLUORESCENT DYES (AIDA) FOR SOLID PHASE AND SOLUTION PHASE SCREENING

TECHNICAL FIELD

The present invention relates to the field of ultra high-throughput screening on the solid support and in homogeneous solution by a novel generic labelling technology. The new labelling technology is based on new chemically stable fluorophores, which possess reactive chemical functionalities for attachment to a solid support and subsequent start of combinatorial synthesis of compound libraries.

BACKGROUND

Three new scientific disciplines show the highest promise of fulfilling the need for increased predictability and for lowering the overall attrition rate of the drug discovery process. (1) Functional Genomics was invented to generate new innovative molecular targets. (2) Combinatorial Chemistry provides increasingly efficient ways to generate molecular diversity with which to probe the targets. (3) High-throughput screening (HTS) plafforms provide efficiency and quality in finding potential lead compounds. High throughput screening within most pharmaceutical companies currently involves performing several million assays per year. Meanwhile, HTS has become a discrete discipline assimilating biochemistry, biophysics and cell/molecular biology combined with detection/liquid handling technologies and automation processes. With all the phantastic oportunities these new scientific disciplines offer, it became already clear, that the time consuming process in functional genomics is the identification of the physiological function of a new protein. Whereas combinatorial chemistry approaches help to synthesize a multifold of compounds during the time needed for classical synthesis, it is known now that between 5 and 10 times the number of assays are needed to identify hit compounds from screens. The challenge the community of applied science is currently faced with, is to fully exploit the advantages of (1) and (2) in a timely manor by speeding up the process of synthesis, protein function identification and screening. The current invention opens a new possibility for integrating the advantages of combinatorial chemistry and genomics with HTS by providing the efficiency needed for screening compounds directly on the solid support. Target macromolecules of even unknown functionality can be tested for their direct binding affinity to compounds of interest. The new fluorescent chemistry, generically described as AlDA-chemistry in the following, is suitable also to screening assays in homogeneous solution, either by direct application of the compounds conjugated to the AlDA chemistry or by cleavage of the AlDA conjugates from the solid support by well known chemical or photophysical means. After the release of the AlDA conjugated "binder" identified in a solid-phase screening technology, the affinity to the macromolecule of interest can be determined by conventional ensemble averaging fluorescence spectroscopic techniques in assay volumes used in microtiter plates. In addition, single molecule spectroscopic techniques performed in microliter volumes and applied in so called nanocarriers can be used.

SUMMARY OF THE INVENTION

The invention refers to specific fluorescent dyes, which can be used in high throughput screening both, on the solid phase as well as in homogeneous solution. The new fluorescent dyes generically referred to as AlDA chemistry is suitable for various methods of solid phase and solution phase organic chemistry for synthesis of molecules to be investigated for therapeutic use in disease states. As used herein, "AlDA" is an abbreviation for arylindazol compounds or derivatives described herein. The molecules of therapeutic interest can be synthesized as fluorescent conjugates by two methods: (a) a solid support is loaded with a cleavable linker (acid-, base-, redox- or light sensitive) to which initially the fluorescent dye is attached. The dyes possess a second functionality, which serves as attachment point for spacer elements. The spacer bears a further functional group which is used as starting point of the synthesis of the molecules to be investigated; (b) the fluorescent dye can also be introduced as end-cap in the last synthesis step of a reaction sequence. The specific dyes described in the invention are chemically stable under a broad range of reaction conditions usually applied in solid phase and solution phase organic chemistry. The conjugates emit fluorescence in the visible and UV-spectrum on excitation at wavelengths of their absorption. These fluorescence properties allow for multiple applications in fluorescence based processes for the identification of inhibitors of molecular interactions and for the identification of molecules which bind to target macromolecules like peptides proteins, nucleic acids, carbohydrates etc. The fluorescence detection technologies used for monitoring binding of AlDA-conjugated compounds to macromolecules include conventional macroscopic techniques (ensemble averaging) which detect changes in fluorescence intensity, anisotropy(polarization), fluorescence resonance energy transfer, fluorescence lifetime, rotational correlation time as well as single molecule spectroscopic techniques (SMS). SMS include excitation by one or two laser wavelengths including laser lines at 325 nm, 351 nm, 453 nm, 488 nm, 514 nm, 543 nm, 632 nm and other excitation possibilities . The fluorescence light emitted from single molecules diffusing through a confocal focus as applied in single molecule spectroscopy passes through one or two filters, and polarisers before the light reaches the avalanche photodiode detector. The comprehensive detection technologies in SMS to be applied to AlDA include translational diffusion, rotational diffusion, fluorescence lifetime, fluorescence brightness, spectral shifts, fluorescence energy transfer, triplet transition probabilities and multiplex detection. The dyes show sufficient stability in chemical transformations, have little triplet state formation and are not photoreactive under the conditions used for detection of binding events to biomolecules, making them to an excellent tool for combination of combinatorial chemistry (solid phase and solution phase chemistry) and biological investigations (ultra high throughput screening).

Uses of the dye include solid phase and solution phase organic chemistry, low molecular weight compound labelling, peptide labelling, protein labelling, optical spectroscopy and fluorescence. Synthesis of functionalized dyes and of dye conjugates (on solid support and in solution) are disclosed.

DETAILED CHEMICAL ASPECTS OF THE INVENTIONS

A first aspect of the invention is directed to a fluorescent dye represented by formula (I)

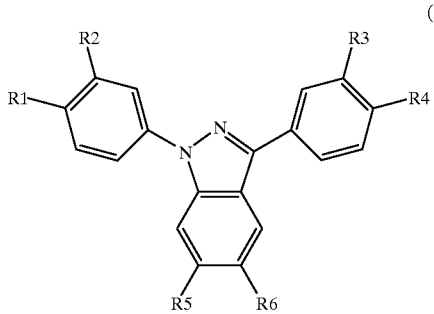

(Formula (I))

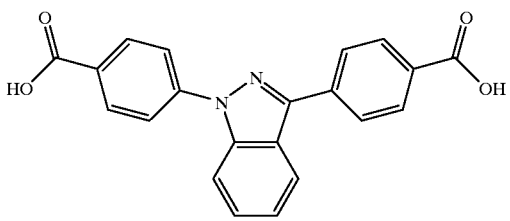

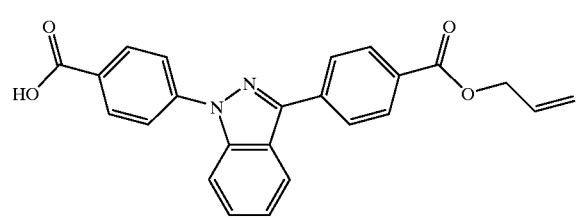

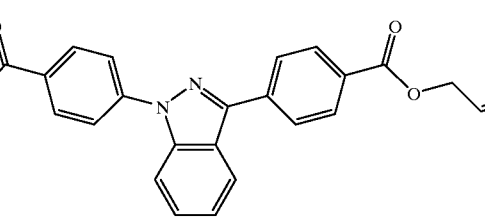

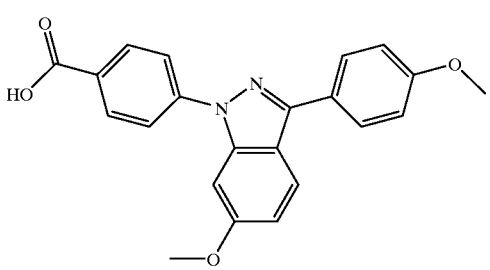

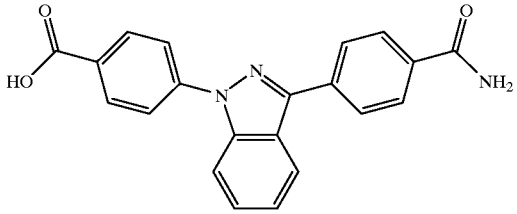

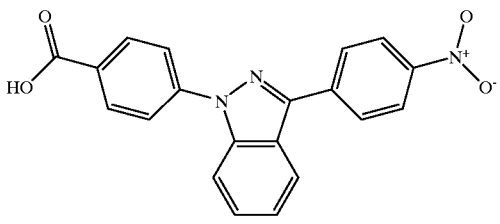

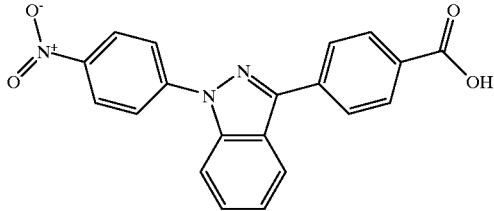

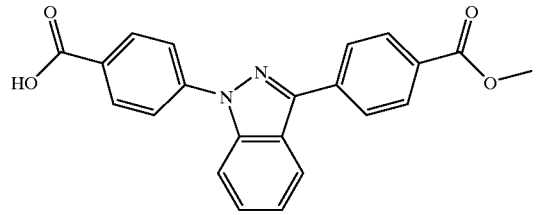

Wherein one of the radicals $R^1$ or $R^2$ and one of the radicals $R^3$ or $R^4$ is hydrogen and the other is independently —COOH, —COOR$^7$, —CONH$_2$, —CONR$^8$R$^9$, —CONH(CH$_2$)$_n$OH, wherein n=2–8, —CH$_2$OH, —CH$_2$NH$_2$, —NO$_2$, NR$^{10}$R$^{11}$, NHCOR$^{12}$, Cl, Br, F, —CF$_3$, O(C$_1$–C$_4$)-alkyl (optionally substituted by methyl or phenyl at any of the carbons C$_1$–C$_4$), —N=C=O, N=C=S, —SO$_3$H, —SO$_2$NH(CH$_2$)$_n$NH$_2$, (C$_1$–C$_4$) alkyl, (C$_1$–C$_{16}$)-alkyl substituted at the terminal carbon with —COOH, —COOR$^7$, —CONH$_2$, —CONR$^8$R$^9$, —CONH(CH$_2$)$_n$OH, wherein n=2–8, —CH$_2$OH, —CH$_2$NH$_2$, —N=C=O, N=C=S, —SO$_3$H, —SO$_2$NH(CH$_2$)$_n$NH$_2$, —CONH(CH$_2$)$_n$NH$_2$, wherein n=2–8, and the NH$_2$-group could also be substituted by (C$_1$–C$_4$) alkyl or a commonly used amino protecting group such as tert-butyloxycarbonyl, 9-fluorenylmethoxycarbonyl, phthalimido, trifluoroacetamido, methoxycarbonyl, ethoxycarbonyl, benzyloxycarbonyl, allyloxycarbonyl, 2,2,2-trichloroethoxycarbonyl, 2-(trimethylsilyl)ethoxycarbonyl, and one of the radicals $R^5$ or $R^6$ is hydrogen and the other is hydrogen, halogen, O(C$_1$–C$_4$)-alkyl (optionally substituted by methyl or phenyl at any of the carbons C$_1$–C$_4$), —NO$_2$, NR$^{10}$R$^{11}$, NHCOR$^{12}$, (C$_1$–C$_4$) alkyl, (C$_1$–C$_{16}$)-alkyl substituted at the terminal carbon with —COOH, —COOR$^7$, —CONH$_2$, —CONR$^8$R$^9$, —CONH(CH$_2$)$_n$OH, wherein n=2–8, —CH$_2$OH, —CH$_2$NH$_2$, —N=C=O, N=C=S, —SO$_3$H, —SO$_2$NH(CH$_2$)$_n$NH$_2$, —CONH(CH$_2$)$_n$NH$_2$, wherein n=2–8, and the NH$_2$-group could also be substituted by (C$_1$–C$_4$) alkyl or a commonly used amino protecting group such as tert-butyloxycarbonyl, 9-fluorenylmethoxycarbonyl, phthalimido, trifluoroacetamido, methoxycarbonyl, ethoxycarbonyl, -benzyloxycarbonyl, allyloxycarbonyl, 2,2,2-trichloroethoxycarbonyl, 2-(trimethylsilyl)ethoxycarbonyl $R^7$ is a commonly used carboxyl protecting or carboxyl activating group, such as succinimidyl, azido, phenyl, 4-nitrophenyl, and pentafluorophenyl for activation and methyl, β-substituted ethyl, 2,2,2-trichloroethyl, tert-butyl, allyl, benzyl, benzhydryl, 4-nitrobenzyl, 2-(4-toluenesulfonyl)ethyl, silyl, 2-(trimethylsilyl)ethyl, MEM, MOM, BOM, MTM, and SEM for protection, respectively.

$R^8$ or $R^9$ is hydrogen and the other is lower alkyl (C$_1$–C$_4$), phenyl, benzyl, or $R^8$ and $R^9$ are part of a 5 or 6 membered such as in piperazine $R^{10}$ and $R^{11}$ are independently hydrogen, (C$_1$–C$_4$) alkyl $R^{12}$ is (C$_1$–C$_{10}$) alkyl, phenyl, which both can be substituted by (C$_1$–C$_4$) alkyl, protected (suitable protecting groups are mentioned above) amino group or halogen.

Preferred embodiments of these aspects are fluorescent indazole dyes represented by the following structures:

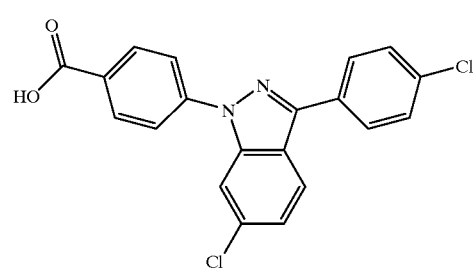
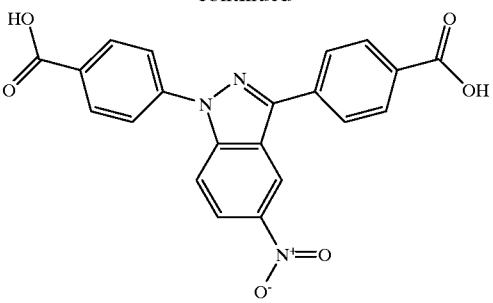
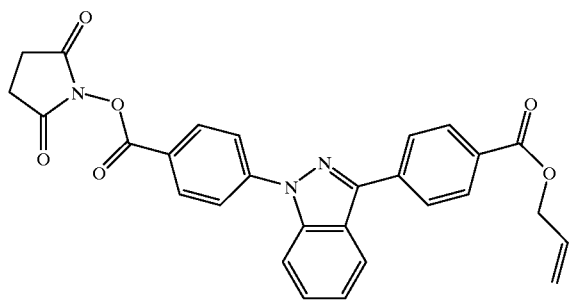
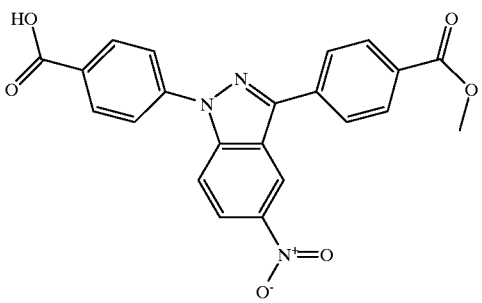
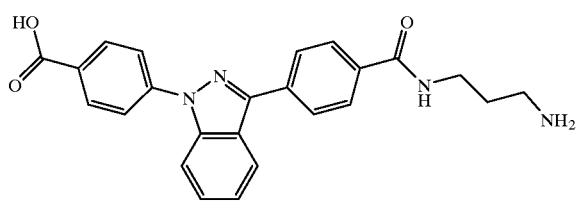
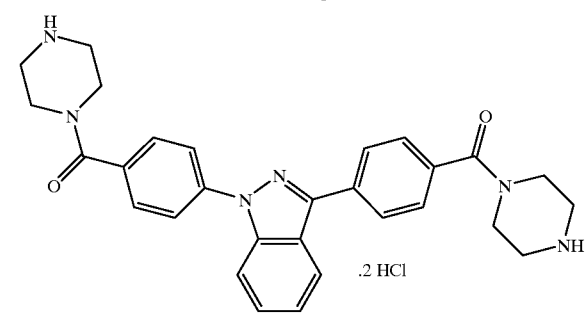
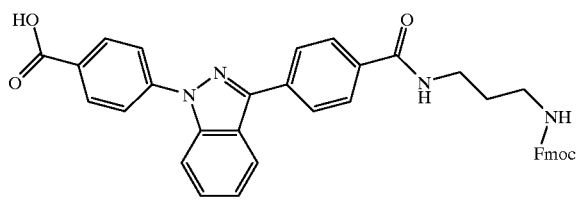
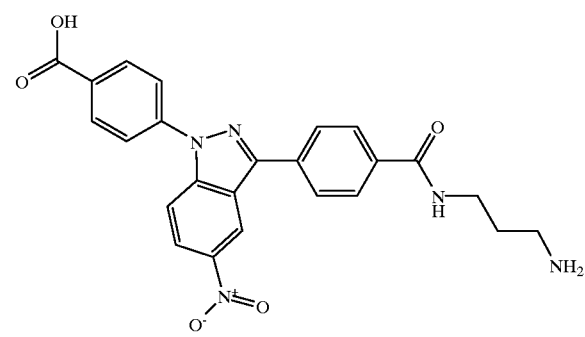
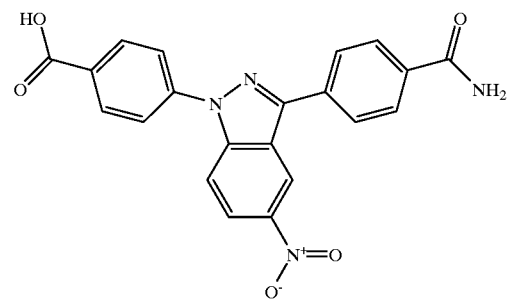
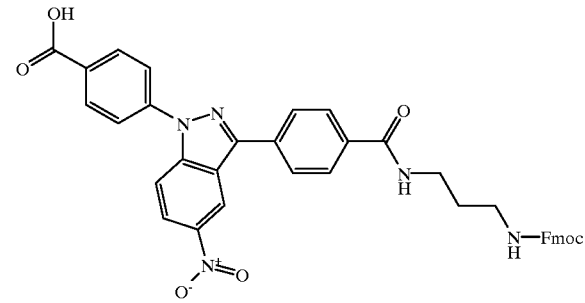
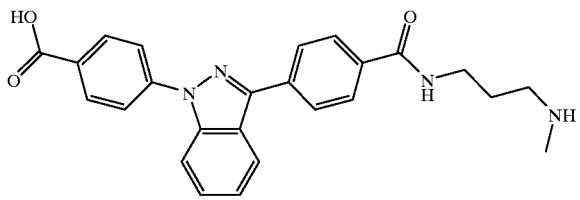

-continued

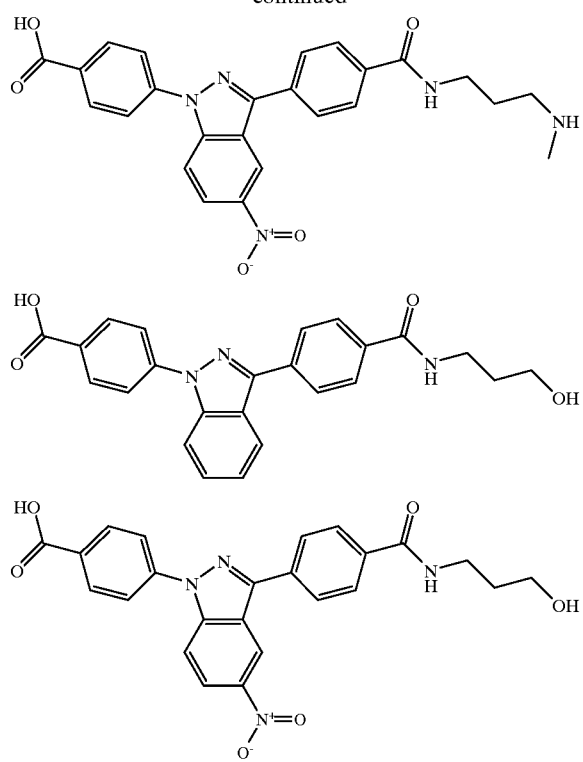

Another aspect of the invention is directed to fluorescent conjugates represented by formula (II–III)

A—B—D—C—D'—E (Formula (II))
A—B—D—E—D'—C (Formula (III))

wherein

A is a solid support selected from standard materials applied in solid phase and solution phase organic chemistry (e.g. functionalized polystyrene based resins, polyacrylamide based polymers, polystyrene/polydimethylacrylamide composites, PEGA resins, polystyrene-polyoxyethylene based supports, Tentagel, PEG-polystyrene graft polymeric supports, glass surfaces, functionalized surfaces, materials grafted with functionalized surfaces, or polyethylenglycol).

B is a linker allowing cleavage of fluorescent conjugates of formula (II–III) for liberation of the D—C—D'—E or D—E—D'—C fragment, respectively. B is selected from the known acid labile, base labile, light labile, redox-labile, and masked linkers applied in combinatorial synthesis, peptide synthesis, and oligonucleotide synthesis (e.g. benzyl, benzhydryl, benzhydryliden, trityl, xanthenyl, benzoin, silicon, or allyl based linkers).

C is a compound selected from formula (I)

D and D' are independently a bond or a spacer selected from α,ω-diamino-alkanes, diaminocyclohexyl, bis-(aminomethyl)-substituted phenyl, α-amino-ω-hydroxy-alkanes, alkylamines, cyclic alkylamines, cyclic alkyl-diamines or amino acids without or with additional functionality in the side chain.

E is the molecule to be investigated e.g. a low molecular weight compound, a peptide, a protein, a carbohydrate, a nucleic acid, or a lipid bearing a functional group for attachment.

Conjugates of formula (II) can be generated via two independent protocols: (a) by de novo synthesis of molecule E, such incorporating a functional group of the spacer D' of the A—B—C—D' or A—B—D—C—D' fragment, respectively, (b) by attachment of a pre-built molecule E containing a suitable functional group for coupling to the A—B—C—D' or A—B—D—C—D' fragment, respectively (e.g. an amino or carboxy terminus).

Conjugates of formula (III) can be generated either by de novo synthesis of molecule E starting with the A—B or A—B—D conjugate, and subsequent capping with a D'—C or C fragment, or by attachment of a pre-built molecule E containing suitable functional groups for coupling to the A—B or A—B—D, and D'—C or C fragment, respectively (e.g. an amino and carboxy terminus).

Preferred compounds of formula (I) used as C for synthesis of conjugates represented by formula (II) are:

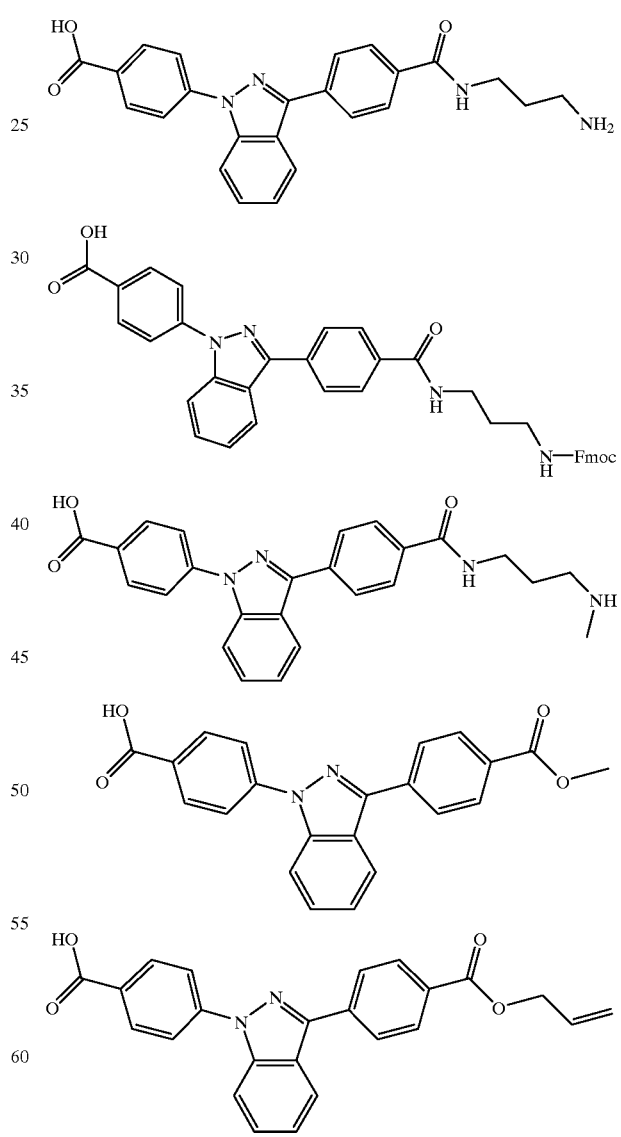

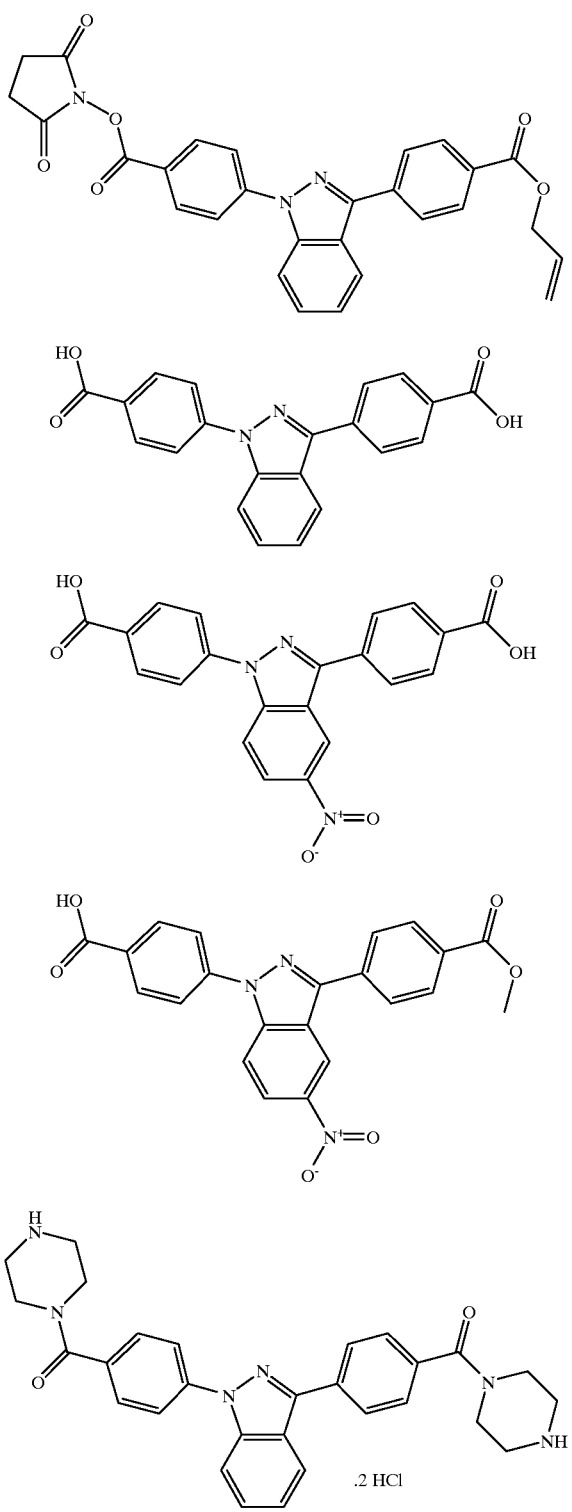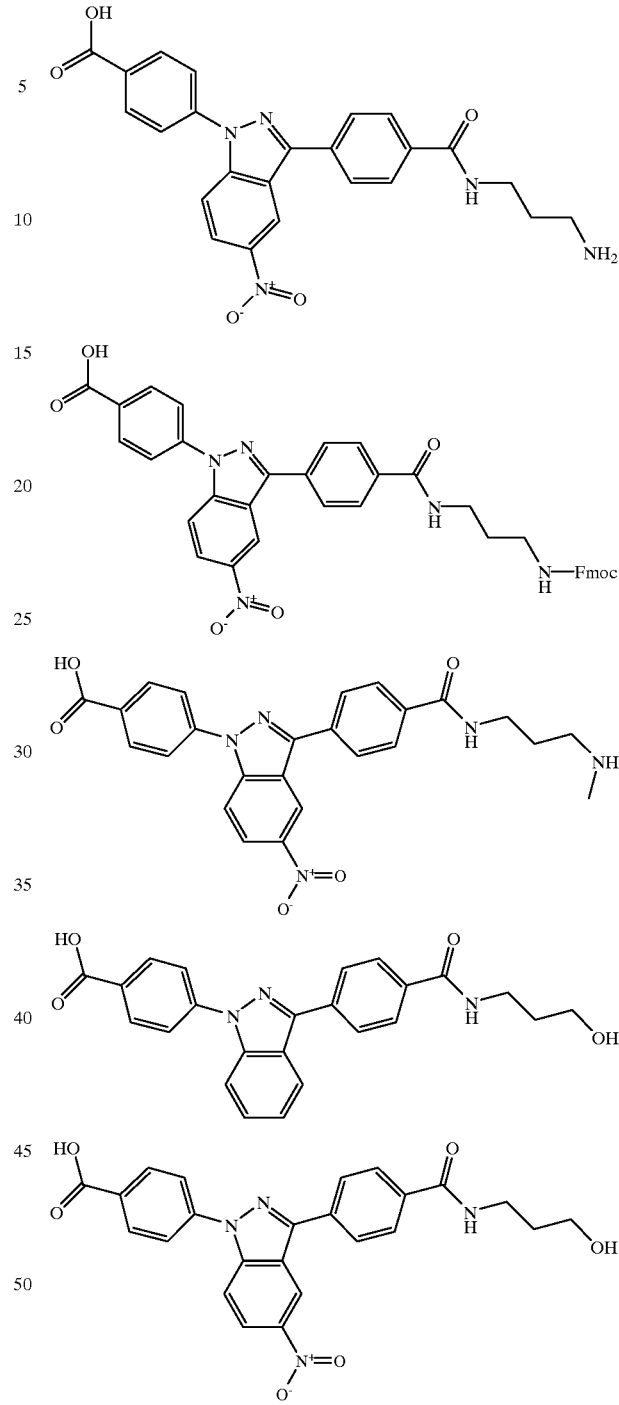
Preferred compounds of formula (I) used as C for synthesis of conjugates represented by formula (III) are:

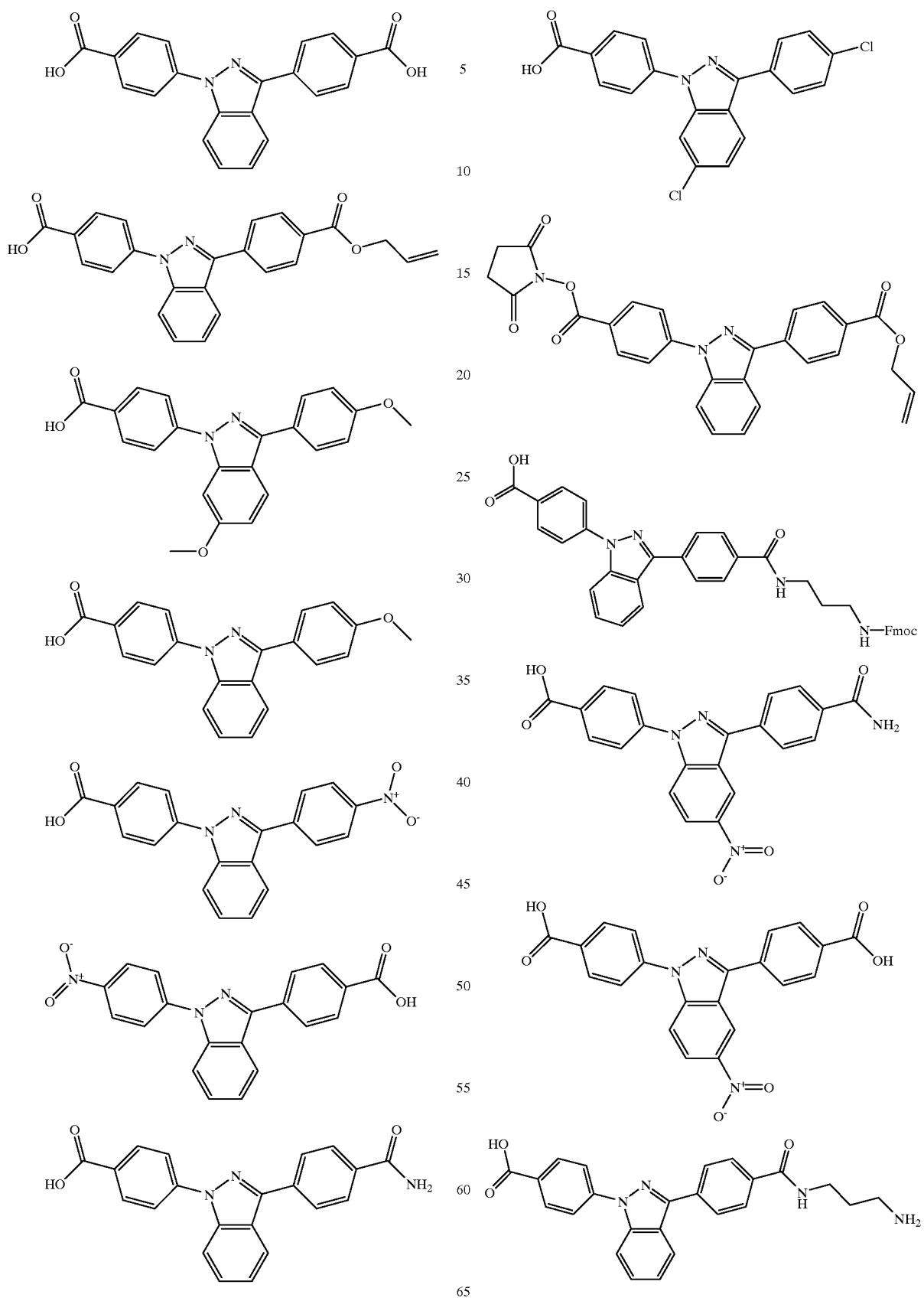

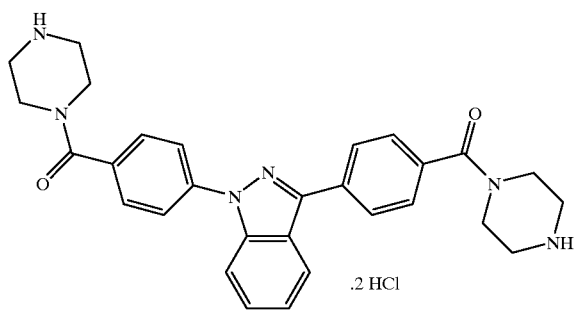
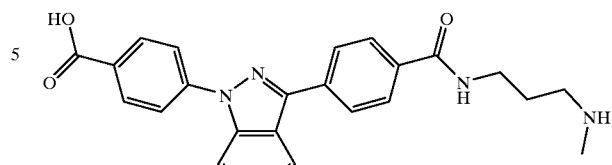
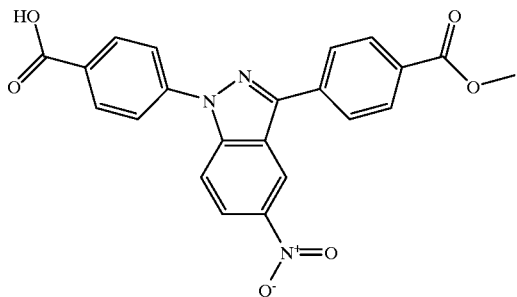
Preferred conjugates of formula II are represented by the following structures:
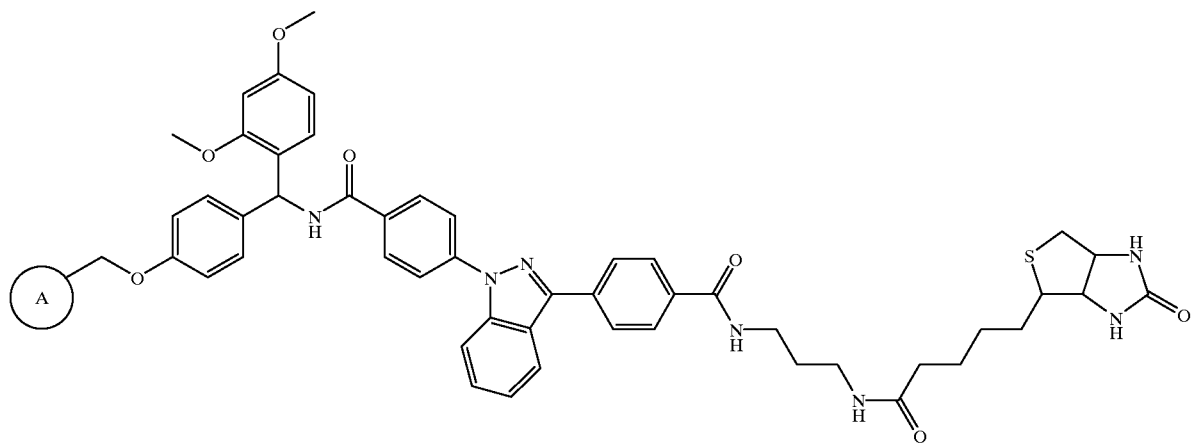
A—B—C—D'—E
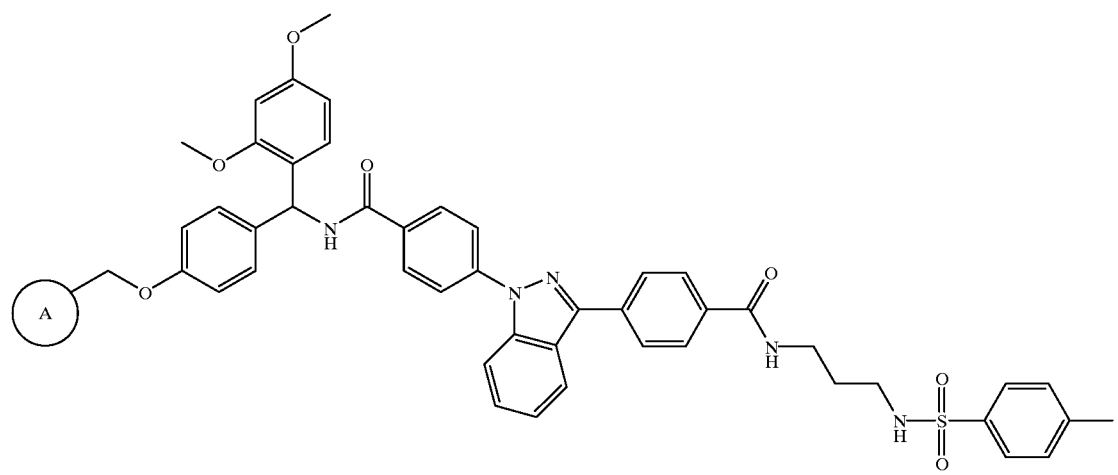

Preferred conjugates of formula III are represented by the following structures:

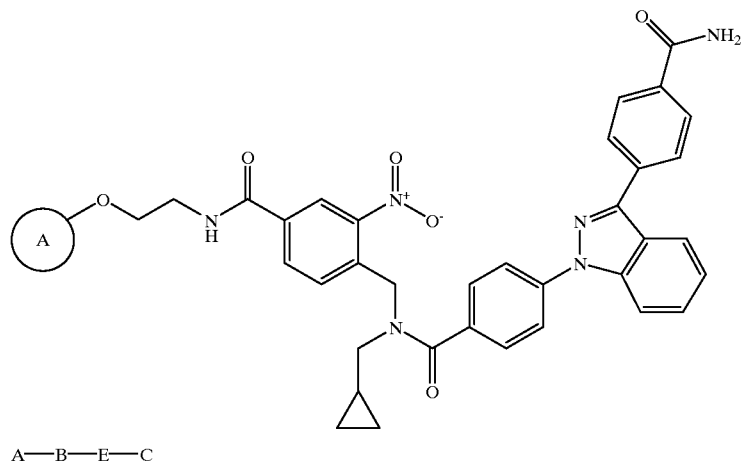

A—B—E—C

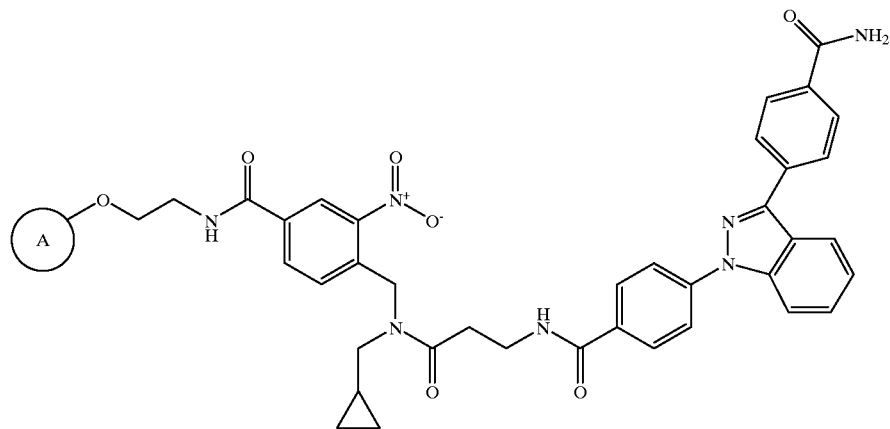

A—B—E—D'—C
A—B—D—E—C

A further aspect of the invention is directed to AlDA conjugates represented by formula (IV):

E—D'—C (Formula (IV))

wherein

E is the molecule to be investigated e.g. a low molecular weight compound, a peptide, a protein, a carbohydrate, a nucleic acid, or a lipid bearing a functional group for attachment.

D' is a bond or a spacer selected from α,ω-diamino-alkanes, diaminocyclohexyl, bis-(aminomethyl)-substituted phenyl, α-amino-ω-hydroxy-alkanes, alkylamines, cyclic alkylamines, cyclic alkyldiamines or amino acids without or with additional functionality in the side chain.

C is a compound selected from formula (I).

Preferred compounds of formula (I) used as C for synthesis of conjugates represented by formula (IV) are as given for formulas II and III.

Preferred compounds of formula (IV) are represented by the following structures:

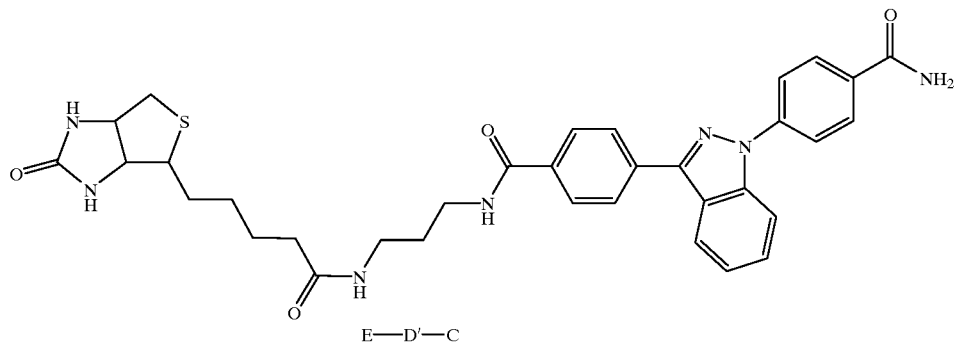
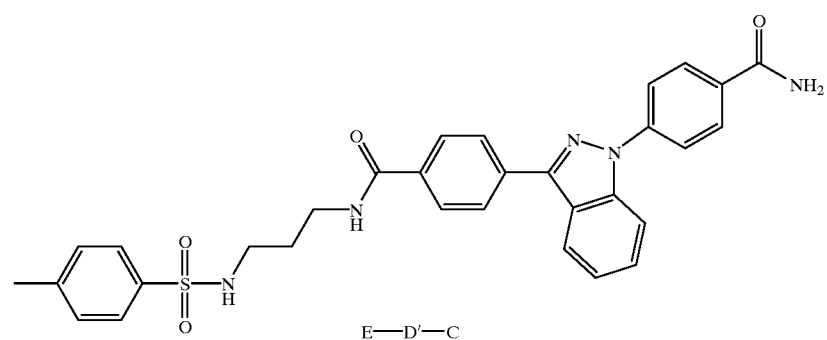
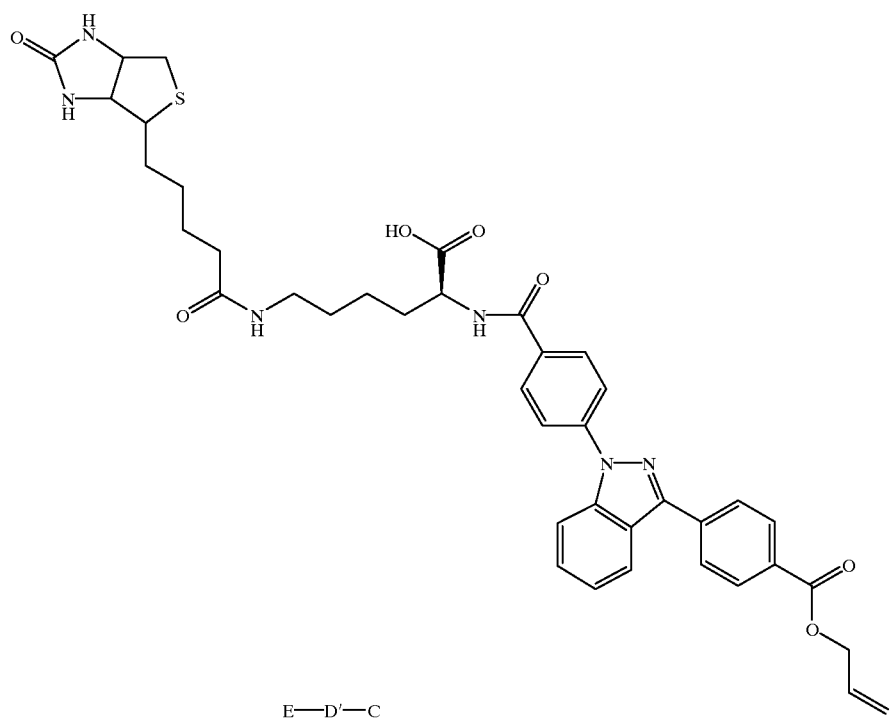

-continued

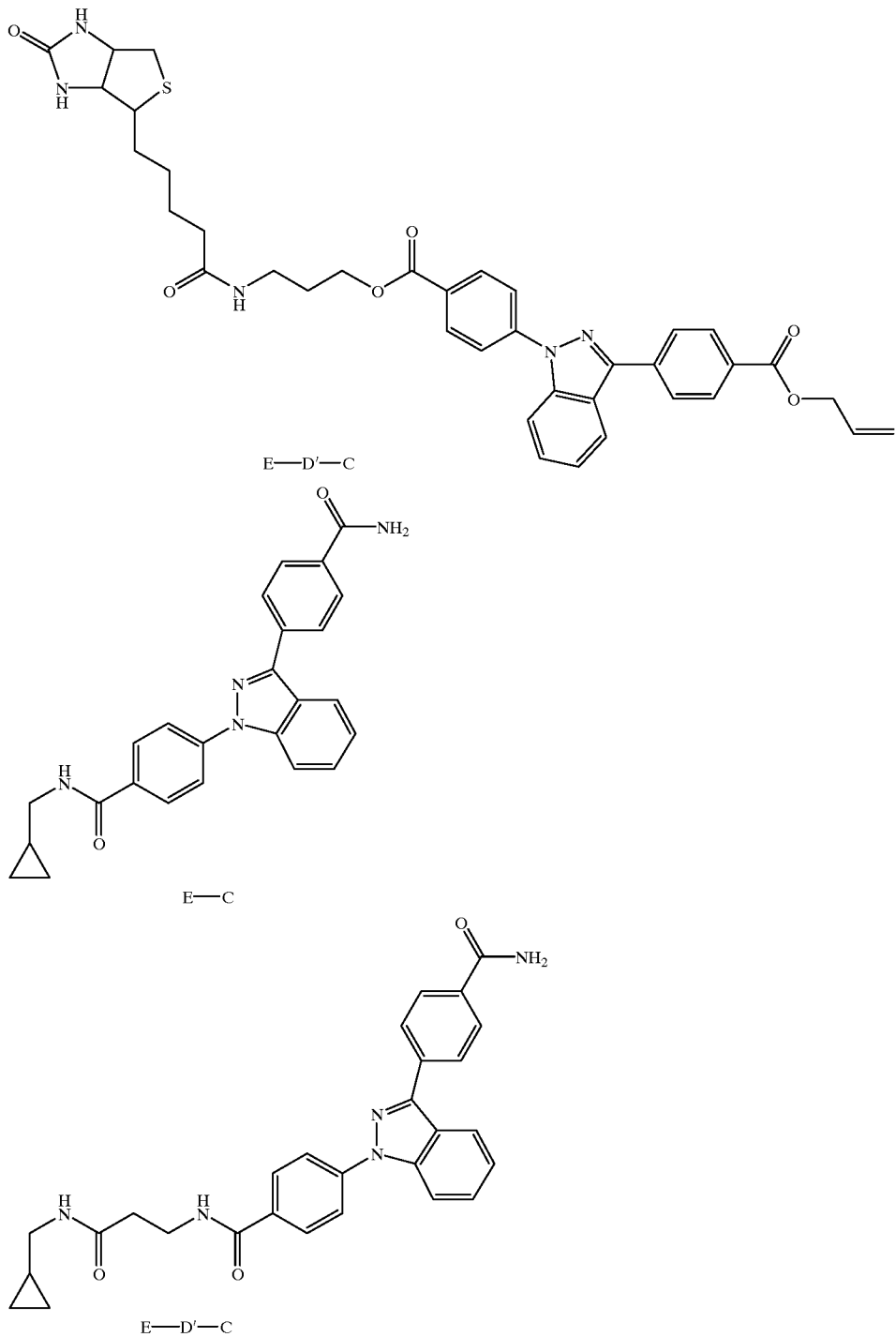

DETAILED METHODOLOGICAL/ TECHNOLOGICAL ASPECTS OF THE INVENTION

Among the many feasibly applications based on AlDA dye molecules, the most promising detection procedures are the following:

(1) AlDA molecules on the solid support cannot be excited to fluorescence by the conventional Ar-ion and HeNe laser lines starting at 453 nm and predominantly using 488 nm, 514 and 543 nm wavelengths to excite dye molecules like fluoresceins or rhodamines etc. AlDA dyes can therefore be used as "silent" fluorescence markers on the solid support without interfering with any kind of detection technology using red (>453 nm) fluorescence.

(2) Once cleaved from the solid support or used on soluble compounds, directly or after cleavage, the AlDA marker can be excited with a UV-laser at 325 or 351 nm excitation source to be detected by various methods used in fluorescence spectroscopy.

(a) In conventional cuvettes used for fluorescence experiments or in microtiterplates, the binding of AlDA-containing compounds to target macromolecules can be detected by the reduction in rotational frequency. The detection parameter applied is the rotational correlations time in time-resolved fluorescence equipments (using the single-photon-counting or phase domain detection modes) or by anisotropy/polarisation in continous wave=prompt=steady state fluorometers.

(b) In single molecule fluorescence experiments the reduction in translational diffusion time determined from autocorrelation calculations on the time trace of fluorescence fluctuations is the analogous detection parameter.

(3) With excitation wavelengths ranging approximately from 300 nm to 400 nm the emission wavelengths of AlDA dyes are usually very broad reaching from approximately 350 nm to 600 nm. It is well known in the literature that UV-excitable dyes show strong environmental sensitivity. By various different kinds of photophysical interactions with binding partners like proteins the fluorescence emission of these dyes including AlDA show quenching or enhancement of fluorescence by various different mechanisms including charge transfer and electron transfer mechanisms. This results in a change of quantum yields or a shift of the spectra to longer or shorter wavelengths. These signal parameters are used to monitor binding reactions.

(4) For applications with AlDA based dyes another suitable interaction parameter is fluorescence resonance energy transfer (FRET). The range and the shape of the absorption spectra of the stable AlDA conjugates (on solid support as well as in solution) show an excellent spectral overlap with the emission of the fluorescent amino acid tryptophan in proteins. The emission spectra of the AlDA-conjugates (usually between 350 and 600 nm) overlap with various conventionally used fluorescence labels of proteins (e.g. BODIPY, Rhodamine, Fluorescein, Cy). These spectral properties enable detection of binding events between conjugates and biomolecules (labelled or unlabelled) by fluorescence resonance energy transfer from excited tryptophan (donor) to the dye molecule (acceptor) of the conjugate. In a different experimental setup, the fluorescence resonance energy transfer can be established between the AlDA-containing molecule and a fluorescence label (acceptor) conjugated with the biomolecule on excitation of the AlDA (donor). In sum, in macroscopic fluorescence experiments (averaging the signals of many molecules in a cuvette or micro-titer plate), AlDA-conjugates can be used as fluorescence donors or as fluorescence acceptors in FRET experiments on the solid support or in homogeneous solution. Complex formation with tryptophan and/or tyrosine containing proteins can be detected by donor (tryptophan) quenching or acceptor (AlDA) sensitisation. Complex formation with fluorescently labelled macromolecules (labeles include all dyes excitable to fluorescence between 350 nm and 680 nm) can be detected by donor (AlDA) quenching and acceptor (emission energies lower than at 350 nm) sensitisation.

(5) In SMS AlDA-conjugates can also be used as donors and acceptors. The FRET derived quenching or enhancement of the tryptophan, AlDA or red acceptor dye (e.g. Rhodamine) is monitored by the change in molecular brightness. UV-excitation of tryptophans, however is only possible with two- or three photon excitation by pulsed lasers in the femtosecond frequency range, wheras AlDA can be excited by cw-UV-lasers at 325 nm or 351 nm.

(6) The following assay detection schemes are possible with AlDA and SMS.

(6.1) On the solid support:

(a) Silent AlDA-1: The direct detection of binding of fluorescently labelled macromolecules to AlDA containing solid supports applying confocal microscopic techniques like the one described in WO 95/35492 (Eigen, M. & Henco, K., Process and device for selectively extracting components from complex mixtures).

(b) Silent AlDA-2: With fluorescently tagged solid supports containing AlDA on linked compounds the procedure described in 6.1.a. can be applied using two excitation and two detection channels. Whereas the tag on the solid support (e.g. in the interior of a bead) can be excited at 543 nm and detected at 570 to 580 nm, the target macromolecule which is tested for binding to the AlDA-containing compound on the solid support can be excited at 632 nm and detected e.g. between 670 and 690 nm. This dual color excitation and emission method can strongly increase the specificity of the detection of the complex formation on the solid suport by cross-correlating the emission signals of two dyes or by monitoring the coincedence of the two colors on a detection timescale within the scanning confocal focus.

(c) Including AlDA fluorescence-2: The change in molecular brightness can be enhanced by chemically linking AlDA to a second environmentally sensitive molecule as commonly used in conventional fluorescence spectroscopy performed during the synthesis of the compound on the solid support.

(d) Including AlDA fluorescence-3: As generally described in (5), FRET from AlDA to a suitable long wavelength dye which will thereby be sensitized using AlDA UV-excitation can be detected by change in molecular brightness at the emission wavelength of the long wavelength dye. This acceptor sensitization must by photophysical rules include a quenching of the donor signal. The reduction of specific brightness at 351 nm excitation and 400 nm emission wavelengths can therefore be applied as well for monitoring binding reaction with FRET suitable labelled macromolecules.

(e) As changes in molecular brightness of a molecule are very often connected with a change in quantum yield, all the potential possible applications monitoring changes in molecular brightness are detectable also in a time-resolved mode in SMS.

(6.2) In homogeneous solution

Generally all the single molecule spectroscopic detection technologies described in 6.1. can also be applied in solution after cleavage of the AlDA conjugate from the solid support with the exception of 6.1-a.

The invention therefore relates also to a method for identification of an interaction between an AlDA labelled molecule and a binding molecule in homogeneous solution wherein the method comprises the following steps:

Step 1A: Providing an AlDA labelled molecule selected from formula (IV)

Step 1B: Admixing the AlDA-labelled molecule of formula (IV) with a binding molecule; and then Step 1C: selectively detecting a binding event with the AlDA-labelled molecule described in Step 1 B and the binding molecule by methods of fluorescence spectroscopy.

The methods of fluorescence spectroscopy are measurements of

Increase of fluorescence anisotropy/polarisation of AlDA emission in continuous wave=prompt=steady state fluorometers, Increase of rotational correlation time in time-resolved fluorescence equipments, Increase in translation diffusion time in single molecule fluorescence experiments determined from autocorrelation calculations on the time trace of fluorescence fluctuations, Increase or decrease of AlDA fluorescence emission in the wavelength range between 350 and 700 nm with excitation wavelengths in the range between 300 and 400 nm, Fluorescence resonance energy transfer (donor quenching or acceptor sensitisation) from excited tryptophan (donor) in the binding molecule which in this case is a peptide or protein to the AlDA dye (acceptor) in the molecule of the conjugate, Fluorescence resonance energy transfer (donor quenching or acceptor sensitsation) from the excited AlDA dye in the conjugate molecule (donor) to a fluorescent label (acceptor) of the binding molecule which in this case can comprise any compound class.

Furthermore the invention relates to a method for identification of an interaction between an AlDA labelled molecule on the solid support which is conventionally used in solid phase organic chemistry and a binding molecule in homogeneous solution containing the solid support wherein the method comprises the following steps:

Step 2A: Providing an AlDA labelled molecule as conjugate of formula (II or III)

Step 2B: Admixing the AlDA-labelled molecule as conjugate of formula (II or III) with a binding molecule; and then Step 2C: selectively detecting a binding event with the AlDA-labelled molecule described in Step 2B and the binding molecule by methods used in fluorescence spectroscopy resulting in a quantitative signal providing a means to identify the AlDA-linked molecule with the highest binding affinity to the binding molecule, Step 2D: Isolation of the solid support containing the identified AlDA-molecule represented by formula (II or III)

Step 2E:: Selectively detecting a binding event with the AlDA-labelled molecule described in Step 2D and the binding molecule by various methods used in fluorescence spectroscopy described in the procedure 1A–C.

The fluorescence spectroscopic methods in step 2C are

Direct detection of binding of fluorescently labelled macromolecules to AlDA containing solid supports applying confocal microscopic and spectroscopic techniques measurement of enhancement of the change in molecular brightness by chemically linking AlDA to a second environmentally sensitive molecule as commonly used in conventional fluorescence spectroscopy performed during the synthesis of the compound on the solid support, measurement of fluorescence resonance energy transfer: From AlDA to a suitable long wavelength dye which will thereby be sensitised using AlDA UV-excitation detected by change in molecular brightness at the emission wavelength of the long wavelength dye, measurement of fluorescence resonance energy transfer: Reduction of specific brightness of AlDA on the molecule linked to the solid support at 351 nm excitation and 400 nm emission wavelengths, Detection of the change in quantum yield by measuring reduction or increase in molecular brightness by time-resolved single molecule spectroscopy.

POSITIONING OF THE DISCLOSED AlDA CHEMISTRY RELATIVE TO KNOWN INDAZOLE CHEMISTRY AND PHOTOPHYSICS

The invention is directed to fluorescent dyes represented by functionalized 1,3-diaryl-1H-indazoles (AlDA). The present invention allows the synthesis of combinatorial compound libraries with inherent fluorescence label on solid support and in solution. Such labels are powerful tools for detection of binding events of synthesized ligands to biomolecules. Binding events between synthesized molecules and biological targets can be measured by spectroscopic methods as described in the previous section. These experiments can be performed with dye conjugates immobilized on a solid support or in solution.

The molecules described in the invention fulfil several chemical and spectroscopic -requirements for use in the disclosed applications. The parent compound of the disclosed indazole based dyes, 1H-indazole, is a fluorescent molecule with a maximum of absorption at 294 nm and a maximum of fluorescence emission at 298 nm (both values in acetonitrile; Saha, S. K. & Dogra, S. K. J. Photochem. Photobiol., A (1997), 110, 257–266). These spectroscopic properties are not in agreement with the requirements, which a dye has to fulfil for use in the applications described above. Only when the indazole chromophore is extended by appropriate substitution with arylsubstituents (which bear additional functional groups for the synthetic applications of the dyes, as such also contributing to further extension of conjugation) the necessary bathochromic shifts of the absorption maximum as well as of the fluorescence emission maximum can be achieved to provide for the applications described in the former sections. The mentioned synthetic modifications on the parent heterocycle establish the spectral overlap of absorption of the 1,3-diaryl-1H-indazoles (range of absorption maxima 326–361 nm for compounds 4a-I, 8, and 11, respectively) with the emission of tryptophan. Not all modifications with regard to extension of the chromophore of the indazole are beneficial: further extension of the fluorophore represented by the 1,3-diaryl-1H-indazoles with an additionally annellated benzene ring on the heterocycle corroborates the spectral requirements. The absorption spectrum of 4-(3-phenyl-benzo[g]indazol-1-yl)-benzoic acid changes to a naphthalene type spectrum, and the fluorescence emission is dramatically reduced.

The 1,3-diaryl-1H-indazoles show Stokes shifts in the range of 60–200 nm, depending on the substitution pattern, and are characterized by a very broad emission band. Emission maxima are in the range 364–439 nm for derivatives 4a–e, 4g–h, 8, and 11, respectively, and 524–565 nm for derivatives 4f, and 4i-I, respectively, indicating the broad possibilities for tuning the photophysical properties of such a substituted 1,3-diaryl-1H-indazole structure. A detailed spectroscopic characterization of a representative AlDA-derivative (4e; FIG. 1; for structure: scheme 1) is described in example IA. The spectroscopic variability allows for the specific design of interaction or binding assays with labelled or unlabelled target macromolecules in solution and on the solid support. The variability in spectroscopic properties covering an unusual broad range of fluorescence emission wavelengths with an absorption wavelength in the gap region between natural protein fluorescence and conventional dyes used in fluorescence spectroscopy for HTS allows for a unique combination of assay technology, namely (a) fast and efficient screening for binders on the solid support (silent AlDA dye which does not show fluorescence) and (b) immediate confirmation of the identified active hit compounds after cleavage from the support by different possible applications of AlDA fluorescence.

One aspect of the invention, as demonstrated in examples 2A and 3A, below, describes the methods used to show binding of a protein (avidin) to its ligand (biotin) conjugated with a dye molecule of the invention.

The conjugate 11 is used to demonstrate the binding of 11 to avidin by the change of the anisotropy value of free conjugate upon binding to the protein (example 2A). The tight binding of the AlDA-biotin conjugate 11 to avidin is also confirmed by FRET from tryptophans contained in avidin to the AlDA dye, and from the AlDA dye to a BODIPY label on avidin.

Conjugate 8 is synthesized on solid support (example 3B(a)). The emission spectrum of immobilized 8 resembles the one in solution. AlDA-conjugate 8 is cleaved from the resin, and the FRET from tryptophans in avidin, as well as from AlDA to BODIPY on avidin is demonstrated (example 3A). The energy transfer between the AlDA moiety in 8 and the BODIPY fluorescence label on avidin is also studied by time-resolved fluorescence spectroscopy.

Example 2A and 3A exemplify the use of AlDA dyes to report binding events between AlDA-conjugates (8, 11) and unlabelled or labelled biomolecules (avidin, avidin-BODIPY-FL).

To this end, derivatives of 1,3-diaryl substituted 1H-indazoles (4a-I, 5, 6; examples 1B and 2B; schemes 1 and 2) are synthesized possessing (1) a functional group for (a) attachment of the dye to a solid support preloaded with a cleavable linker, or (b) to label a compound library by capping reaction with an appropriate AlDA-derivative, and (2) an additional functional group for conjugation with the ligand. The latter functionality is presented as part of a (variable) spacer element inserted between dye and ligand. The spacer itself is covalently linked to the dye by an amide bond. Among the numerous known possibilities to synthesize the indazole heterocycle (for a review see: Elderfield, R. C. in "Heterocyclic Compounds" ed. Elderfield, R. C., vol 5, John Wiley & Sons, Inc., New York, 1957, p. 162), and more specifically 1,3-diaryl-1H-indazoles, the methods described by Gladstone et. al. (Gladstone, W. A. F. & Norman, R. O. C. J. Chem. Soc. (1965), 3048–52; Gladstone, W. A. F. & Norman, R. O. C. J. Chem. Soc. (1965), 5177–82; Gladstone, W. A. F. et. al. J. Chem. Soc. (1966), 1781–4) enable an efficient access to the desired compounds. The synthesis starts from substituted benzophenones. One of the aromatic substituents of the ketone is finally incorporated into the indazole skeleton, whereas the second one serves as the source for the functionalized 3-arylsubstituent of the indazole. The benzophenone derivatives are first converted to arylhydrazones by reaction with substituted arylhydrazines. The latter are the source for the functional group attached on the 1-arylsubstituent of the final, functionalized 1,3-diaryl-indazole. The benzophenone arylhydrazones are reacted to acetic acid 1-(arylazo)-1,1-diarylmethyl esters by oxidation with lead tetraacetate, following a procedure first described by Iffland (Iffland, D.C. et al. (1961) J. Am. Chem. Soc. 83, 747). The arylazo-acetates undergo ring-closure to indazole heterocycles upon treatment with Lewis acids. The reaction proceeds via an intermediate 1-aza-2-azoniaallene (Wang, Q. et. al. Synthesis (1992), 7, 710-8) and is highly regioselective for the geminal arylsubstituents of the arylazo-acetates competing for ring-closure. Cyclization does not occur into aromatic rings bearing strong electron withdrawing substituents, such as carboxyl-, ester-, amide-, or nitrogroups, respectively. Substitution of the aryl rings, either in position 1 or position 3, of the indazole by a nitro-substituent causes a bathochromic shift of the emission maximum of about 150 nm compared to other substitution patterns investigated (table 1). The nitro induced red shift of the emission of AlDA-derivatives expands the spectroscopic applicabilities described above. The same holds for a nitrogroup attached directly to the nucleus of the heterocycle, but such indazole derivatives are not accessible by the discussed Gladston indazole synthesis, for the reasons given. 5-nitro substituted, functionalized 1,3-diaryl-1H-indazoles can be synthesized by careful nitration of a corresponding indazole as it is exemplified in example 1B(b). Functionalized 1,3-diarylsubstituted indazoles can also be synthesized on solid support starting with immobilized arylhydrazones of appropriate benzophenone derivatives (Yan, B. & Gstach, H. Tetrahedron Lett. (1996), 37(46), 8325–8).

Specifically, an example 3B(a) describes the principle of solid phase synthesis of fluorescent conjugates as represented by formulas (II) and (IV). The spacer bearing AlDA-dye (described in example 2B(b)) is first attached to a linker on a solid support, followed by coupling of the ligand, and subsequent cleavage of the AlDA-ligand conjugate (8). AlDA conjugates as represented by formula (IV) can also be synthesized in solution as it is demonstrated in example 4B(a–c). Synthesized compounds 8 and 9 differ not only in the nature of the spacer introduced for coupling of the ligand (biotin) to the AlDA dye (4e), but also with regard to the arylsubstituents of the indazole. The conjugate to biotin is built up via the 1-arylsubstituent in derivative 8, whereas the ligand is presented on the 3-arylsubstituent in derivative 11. Both geometries can be used for detection of binding events (pseudosymmetry of the AlDA-dyes). The principle of the synthesis of compound libraries of fluorescent conjugates as represented by formulas (III) and (VI) are described in examples 5B and 7B. The AlDA-dye (4c) was introduced in the final step of a reaction sequence, followed by cleavage of the AlDA-ligand conjugates 12a–j, and 14, respectively.

The synthesis of a compound collection of sulfonamides conjugated with an AlDA-dye (13a–d) represented by formulas (II) and (IV) is described in example 6B.

EXPERIMENTAL PROTOCOLS

Part A: Spectroscopic

General

Reagents and Proteins: 10 mM and 5 $\mu$M stock solutions of 4e, 9 and 11 are prepared in THF (4e) or DMSO and kept at 4° C. avidin and avidin-conjugates are purchased from Molecular Probes (Eugene, Oregon): A-2767, unlabelled; A-883, Lucifer Yellow (LY); A-2641, BODIPY FL.

200 $\mu$M stock solutions are prepared in PBS, 0.01% $NaN_3$, or 0.1 M $NaHCO_3$, pH=8.3 (A-2641) and stored at −20° C. Concentrations were determined gravimetrically assuming a molecular weight of 67000 for avidin and conjugates.

For solubility reasons, 4e is spectroscopically characterized in THF. All complexation reactions and fluorescence resonance energy transfer measurements are performed in PBS/5% DMSO at 25° C., unless indicated otherwise.

UV-VIS spectroscopy

UV-Vis absorption spectroscopy is performed on a Cary 1E spectrophotometer. The absorption spectrum of 4e is detected in THF.

Determination of the extinction coefficient (F) of 4e at the absorption maximum at 337 nm:

Three different amounts of the sample (E1=5.751 mg, E2=7.933 mg, E3=10.933 mg) are dissolved in tetrahydrofuran (THF, for UV-spectroscopy, Fluka) to a final volume of 25 mL. This results in concentrations of 577.5 $\mu$M, 796.6 $\mu$M and 1.0979 mM for E1, E2 and E3, respectively. From each stock solution, 5 dilutions with concentrations of 2.5 $\mu$m, 10 $\mu$M, 17 $\mu$M, 25$\mu$m and 35 $\mu$M are made. UV-spectra of each dilution are recorded from 200 to 400 nm, using a quarz cuvette with a pathlength of 1 cm. THF is used as a reference. A linear fit is carried out for each series of measurements. The extinction coefficient ε at 337 nm is given by the slope of the linear regression.

Steady-state fluorescence spectroscopy

Steady-state fluorescence measurements are performed on a SLM 8000C spectro-fluorometer equipped with JD490 photomultipliers and a 450 W Xenon Arciamp (SLM Instruments, Urbana, Ill.).

Steady-state fluorescence spectroscopy of 4e

Steady state fluorescence measurements are carried out in tetrahydrofuran (THF) at 1 μM sample concentration. Spectral bandwidths are set to 1 and 4 nm for excitation and emission, respectively. Spectra are recorded in single photon counting mode. Changes in lamp intensity are corrected with a quantum counter in the reference channel, measured in slow mode. Gain is set to x 100 with a high voltage (HV) of 640 V. Integration time is 2 seconds. For excitation spectra measurements, the emission wavelength is set to 397 nm and the sample is excited from 200 to 400 nm. For recording emission spectra, the sample is excited at 342 nm and the emission is recorded from 350 to 540 nm. The data are averaged over two scans.

Quantum yield determination of 4e [Demas & Cosby, 1971; Chen et al., 1972]

The quantum yield of 4e is determined using chininsulfate as a standard [Melhuish, 1961].

The point of intersection between the UV spectra of 4e and chininsulfate (CS) is determined by measurements of a solution of the two substances on a Cary 1E spectrophotometer. Concentrations were 25 μM in THF for 4e and 50 mM in 1N $H_2SO_4$ for CS. Spectra are recorded from 260 nm to 380 nm using a quartz cuvette with an optical pathlength of 10 mm, and blank corrected by subtracting the solvent absorption. The point of intersection of the two resulting UV spectra is determined to be at 348.3 nm, corresponding to 352.8 nm on the SLM-8000 C fluorometer due to monochromator shifts. The fluorescence emission spectra of 4e and CS are recorded using the same solutions as for the UV-measurements in single photon counting mode. Lamp intensity changes are corrected with a quantum counter in the reference channel, measured in slow mode. Gain is set at x 100, high voltage applied was 830 V. Integration time was 0.5 seconds.

Spectral bandwidths are set at 1 nm for excitation, 2 nm and 4 nm for emission. For the recording of the emission spectra, excitation is set to 352.8 and emission is monitored from 360 to 550 nm for IAE and 360 to 650 nm for CS.

Calculation of $R_0$ (Förster distance) between 4e and N-acetyl-tryptophan amide (NATA)

To calculate $R_0$ between 4e (acceptor) and NATA (donor), the emission spectrum of NATA and the absorption spectrum of 4e are used to determine the region of overlap between 300 nm and 380 nm. The emission spectrum of NATA is measured at a concentration of 15 μM in THF, using a 750 μl quartz cuvette with an optical pathlength of 10 mm. Measuring mode is single photon counting. Changes in lamp intensity are corrected using a quantum counter in the reference channel. The gain is set at x 100, the high voltage applied was 640 V and the integration time is 2 seconds- The fluorescence emission is corrected for photometric accuracy of the system by multiplication with correction factors obtained by standard lamp calibration. Slit widths are set at 1 nm and 4 nm for excitation and emission, respectively. The sample is excited at 293 nm and emission was monitored from 300 to 480 nm.

$R_0$ is calculated using the formula $$R_0 = (9.97 \times 10^3)(J\kappa^2 \eta^{-4} \Theta_{NATA})^{1/6} \text{ Å}$$

where $\kappa^2$ is an orientation factor of the relative orientation in space of the transition dipoles of the donor and acceptor chromophores. For the donor-acceptor pairs that have isotropic rotation on the time scale of the fluorescence lifetime, a value of 2/3 can be used [Chen, 1972].

η is the refractive index of the solvent, in this case THF with a value of 1.4064. $\Theta_{NATA}$ is the quantum yield of the donor, which is taken from the literature as 0.12–0.14 [Szabo & Rainer, 1980; Petrich et.al., 1983].

J is the spectral overlap integral which can be approximated from $$J = SF_{NATA}(\lambda)\epsilon_{4e}(\lambda)\lambda^4 \Delta\lambda \qquad (2)$$

where $F_{NATA}$ is the corrected fluorescence emission of the donor, the sum normalized to unity, $\epsilon_{4e}$ is the extinction coefficient of the acceptor at wavelength λ, and DS is the incremental detection range.

FRET measurements

Spectral bandwidths are set to 8 and 16 nm for excitation and emission, respectively. Measurements are performed at 25° C. in a 750 μL quartz cuvette (10 mm optical pathlength) without stirring after initial mixing. A concentration of 50 nM of 9 or 11 is used for complexation with 1 μM of (fluorescent) avidin. With a dissociation constant in the range of $10^{-5}$ M, as usual for avidin biotin interactions, complete saturation of the labelled biotin platform is achieved. All titrations are performed in magic angle setting, with the emission wavelength set to 500 nm in experiments where the indazole is the acceptor, and with an excitation spectrum recorded from 250 nm to 360 nm. In experiments where indazole is used as donor and Lucifer Yellow or BODIPY FL is the acceptor, the excitation wavelength is set to 338 nm or 325 nm. The fluorescence emission is collected between 360 nm and 700 nm. The spectra are corrected for Raman scattering from the PBS solution, for dilution, and for inner filter effects due to protein additions, The signal is adjusted for lamp intensity changes by ratio mode detection with a Rhodamine B quantum counter in the reference channel. A WG 360 emission cutoff filter is used for straylight reduction. Data are collected in 2 nm increments with 1 second integration time.

Fluorescence anisotropy measurements

Fluorescence anisotropy is calculated according to [Lakowicz, 1983]. Spectral bandwidths are set to 4 and 8 nm for excitation and emission, respectively, with 5 seconds integration time. For calculation of fluorescence anisotropy ten data points are averaged.

Picosecond time-resolved fluorescence spectroscopy

Picosecond time-resolved fluorescence measurements are recorded according to the single photon counting technique [Lakowicz, 1983 p 52–93, 112–153, 156–185]. An $Ar^+$-pumped Ti:Sapphire laser (model MIRA 900, Coherent, Santa Clara, USA) provided under modelocked conditions ultrashort pulses (FWHM=150 fs) with a frequency of 75 MHz. To reduce the repetition rate to 4.7 MHz, a pulse picker (model 9200, Coherent, Santa Clara, USA) is inserted into the beam. The beam is then split to trgger a fast photo diode on the one hand, which yields after discrimination (Ortec pico-timing discriminator 9307, Oak Ridge, USA) the stop signal for the SPC measurements (reverse mode), and to excite the sample on the other hand. The excitation wavelength of 360 nm is obtained by first manually tuning the MIRA 900 to 720 nm and then double the frequency of the beam with the ultrafast harmonic generation system 5–050 (Inrad, Northvale, USA). The excitation power ranged between 0.1–0.3 mW, the full width at half maximum of the instrument response function being 70–80 ps. Fluorescence photons are collected in a Spex 1681 single grating monochromator (Spex, Edison, USA) and detected with the Hamamatsu R3809U microchannel plate (Hamamatsu, Shimokanzo, Japan). The so obtained start signal is preamplified (preamplifier 9306, Ortec, Oak Ridge, USA) and discriminated (discriminator 9307, Ortec, Oak Ridge, USA) before starting the voltage ramp in the time-to-amplitude converter, which is stopped in the reverse SPC mode by the next signal of the photodiode. The voltage values which correspond to the time passed between excitation and emission of a fluorescence photon in a single experiment are stored in the Spectrum Master 921 (Ortec, Oak Ridge, USA) which is connected to the multichannel emulation program Maestro (Ortec, Oak Ridge, USA). SPC raw data are iteratively reconvoluted with the FLA900 program from Edinburgh Instruments (Edinburgh, UK) according to the multiexponential model $$F(t)=A+\Sigma b_i exp(-(t+\delta t)/\tau_i)$$

where A represents the background noise of the experiment, $b_i$ represent the pre-exponential terms of the according fluorescence lifetimes $\tau_i$, and $\delta t$ is an optional temporal shift term to compensate for shifts of the instrument response. Relative amplitudes $B_i$ are obtained by computing $$B_i=[(b_i\tau_i)/\Sigma(b_i\tau_i)]\times 100\ (\%).$$

The time resolved decay of 4e is determined at a concentration of 25 $\mu$M in THF. Excitation is from 350 nm 380 nm, fluorescence emission is detected at 400 nm with slit widths set to 0.5 nm. Mean width at half maximum of the laser pulse is 130 fsec, of the excitation pulse 65 psec. 15 000 counts are collected in the maximum.

EXAMPLE 1A

Detailed spectroscopic characterization of selected example 4-[3-(4-allyloxycarbonylphenyl)-1H-indazol-1-yl]-benzoic acid (4e)

The AlDA derivative 4e shows absorption maximum at 342 nm and a maximal emission intensity at 403 nm. The compound has a large Stoke shift of about 60 nm and is energetically ideally located between emission of tryptophans in most macromolecular environments and many fluorophores which are commercially available and used as tracers in biochemistry (FIGS 1–2). The almost perfect overlap between the absorption and fluorescence excitation spectra indicates low probability of photochemical and photophysical effects in the excited state.

The absorption coefficient, $\epsilon$, at 337 nm is 29926 $M^{-1}$ $cm^{-1}$ which is about 50% of the value known from fluorescein or rhodamine derivatives, but high enough to serve as acceptor in FRET measurements in the nanomolar concentration range. The quantum yield of 4e,$Q_{4e}$, is 0.591. In comparison to tryptophan ($\approx$0.1) or fluorescein (in organic solvents 0 0.9, linked to proteins or RNA$\approx$0.2–0.4), for a small compound, like 4e, this is a surprisingly high quantum yield suggesting good fluorescence donor properties.

Förster distance to NATA $R_0$ is defined as the distance at which the transfer rate (kT) is equal to the decay rate of the donor in the absence of acceptor. At this distance one-half of the donor molecules decay by energy transfer and one-half by the usual radiative and non-radiative processes. Therefore $R_0$ can be used to check whether indazole derived platform molecules can be used as donor or acceptor in energy transfer experiments in a common situation of distances in protein ligand interactions.

The $R_0$ value of the dye pair 4e and NATA is between 25.2–26.3 Å. With average linker distances between 4 and 10 Å separating the fluorescent indazole tracer from the potential inhibitor, it is very likely that a tryptophan in a substrate binding site is within another 15–20 Å. On the other hand, labeling frequency for external tracers can be adjusted to obtain at least one molecule of the label within 20 Å of the ligand binding site.

AlDA derivative 4e showed a monoexponential decay with a fluorescence lifetime $\lambda_1$ of 1.055±0.117 nsec with a relative amplitude of 99.73 %.

Conclusion: 4e is photophysically and photochemically stable with promising spectroscopic characteristics as fluorescent linker molecule for detection of ligand binding to target proteins.

EXAMPLE 2A

Detection of binding of AlDA-biotin conjugate triethylammonium; (2{4-[3-(4-allyloxycarbonylphenyl)-1H-indazol-1-yl]-benzoylamino}-6-((+)-biotinoylamino)-hexanoate (11) to avidin .

With a $K_d$ of 1.3×10$^{-15}$ M at pH 5 the avidin-biotin complex represents one of the most stable biomolecular interactions known. Both components are extensively characterized. To investigate the properties of AlDA dyes as reporter or detector of interactions with a protein binding site, biotin therefore represents an ideal ligand to mimic a potential inhibitor. The binding site for biotin in avidin comprises 4 tryptophans. Two, tryptophan 70 and 97 are within 5 Å from the biotin in the binding pocket. Tryptophan 10 is 12 Å in distance from biotin, tryptophan 110 in 20 Å, respectively 11 was evaluated for its spectral properties in PBS buffer and for the overlap with the tryptophan, Lucifer Yellow and BODIPY-FL fluorescence in avidin (FIGS. 2b, 2e, 2h).

Figure 2A:
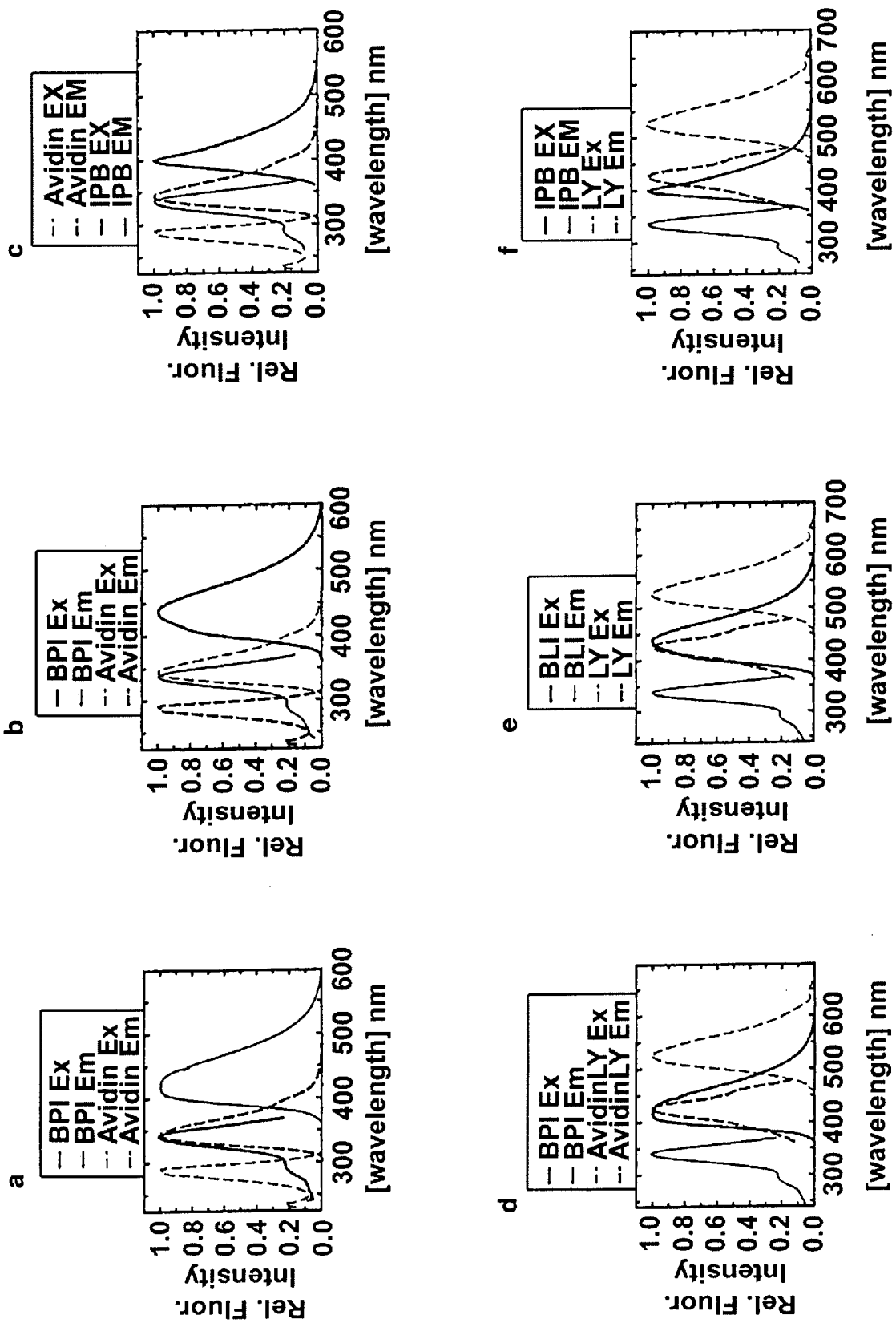
Figure 2B:
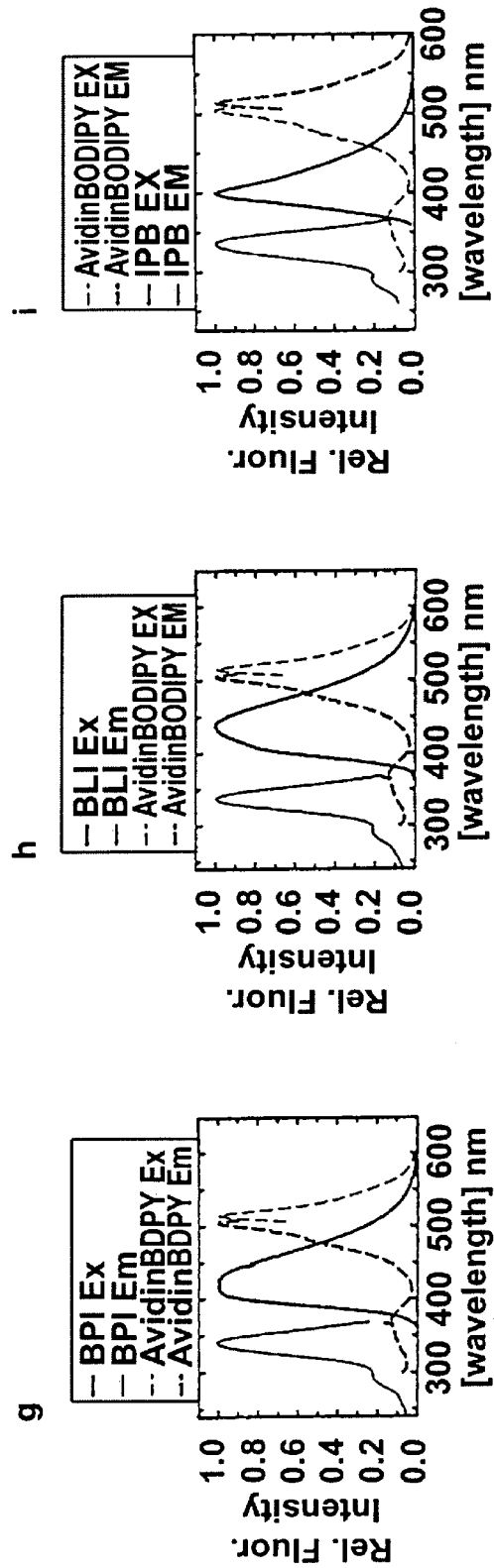

FIG. 2b: Excitation and emission spectra of 11 and avidin showing the overlap between tryptophan emission and excitation spectra of 11.

AlDA derivative 11 has very broad fluorescence emission bandwith with about 50% of emission intensity at 500 nm. The spectral overlap between the tryptophan emission in avidin and the absorption of 11 is almost perfect.

FIG. 2e: Spectral overlap of 11 with Lucifer Yellow labelled avidin. Lucifer Yellow was chosen as possible acceptor for the indazoles because of its absorption between 400 and 500 nm. The overlap with the emission spectrum of 11 in water is almost quantitative.

BODIPY FL absorbs between 480 and 500 nm with an approximately tenfold higher extinction coefficient than Lucifer Yellow. It can be used as check for the relative importance of the extent of the overlap integral in relation to $\epsilon$.

Conclusion: The spectral overlap integral between donor (tryptophan) and acceptor (Lucifer Yellow, BODIPY FL) labels in avidin and the fluorescent AlDA molecule show the ideal energetic position of the indazole for interaction studies. It therefore remains a sole question of distance and non-radiative depopulation terms, whether efficient energy transfer will take place or not.

AlDA conjugate 11 - Avidin Complexes (a) Fluorescence anisotropy of 11 as signal for the biotin binding to avidin in the model system.

AlDA conjugate 11 at a concentration of 50 nM, had a basic fluorescence anisotropy of 0.034 when monitored at the excitation wavelength of 338 nm and the emission maximum of 438 nm. This value is indicative for a small monomeric molecule rotating free in solution. When bound to avidin added in excess of 1 $\mu$M, the anisotropy value was 0.151 (+444%) representing the fixation of the indazole moiety attached to biotin at or near the binding site on avidin. When 1 μM of the BODIPY-FL labelled avidin was used as substrate the r-value was 0.100. This reduced change in anisotropy probably reflects the lower affinity of the BODIPY-FL labelled avidin as compared to the unlabelled material.

(b) Resonance Energy Transfer experiments with 11 as donor or acceptor.

FIG. 3*a* shows the fluorescence excitation spectra of 50 nM of 11 and 1 μM of unlabelled avidin. An emission wavelength at 480 nm was chosen because the tryptophan fluorescence of avidin had almost reached the baseline level at this emission energy, resulting in only minor avidin fluorescence contribution between 250 and 370 nm. The difference spectrum: $[|(11_{(free)})+|(avidin_{(free)})|]-|(11-avidin_{complex})$, FIG. 3*a* curve 5, indicates that the fluorescence of 11 is quenched by about 25.5% by complexation in the avidin binding site. This quenching effect can be attributed to all radiative and non-radiative processes occurring to 11 in the vicinity of the tryptophans in the binding cleft. Corresponding to the ratio of the negative and positive areas under the fluorescence difference curve (black), 62% of this total quenching effect is fluorescence resonance energy transfer. From 250 to 305 nm the enhancement of the tryptophan and tyrosine fluorescence intensity is 72% based on the sum of 11 and avidin.

Conclusion: When 11 is used as acceptor and protein fluorescence in avidin as donor, both an energy transfer to, and a quenching effect on 11 can be used as a signal for the complex formation.

FIG. 3*c* shows the fluorescence emission spectra of 50 nM of 11, 1 μM avidin-BODIPY-FL, the complex- and the relevant difference spectra. In these experiments 11 was used as donor and BODIPY-FL as acceptor. At an excitation wavelength of 338 nm the emission of 11 between 360 nm and 516 nm is strongly quenched by approximately 80% in the complexed form. The standard definition for energy transfer efficiency, $E=1-F_{da}/F_d$, would result in E≅0.8. For intermolecular FRET measurements or for intramolecular FRET determinations where a second component induces potential conformational changes in the binding sites this "classical" definition for E is not valid. The approximately 80% reduction in signal intensity of 11 can be caused either by FRET or from local quenching of the fluorescence of 11 mainly by ground state interactions. However, a small enhancement in BODIPY-FL -fluorescence intensity between 500 and 600 nm, where energy transfer becomes visible, suggests ground state complexation to be the main reason for the quenching effect. However, it can not be excluded, that the BODIPY-FL label looses its excitation energy by non-radiative decay processes, although most of the emission energy of 11 was absorbed by BODIPY-FL. The extinction coefficient of approximately 90 000 M$^{-1}$ cm$^{-1}$, determines that the quenching effect of almost 80% on 11 between 360 nm and 516 nm is an extremely efficient signal for biotin interaction with avidin monitored by 11 at wavelengths between 440 nm and 500 nm. Due to the broad fluorescence emission of 11 in water the detection wavelength can be shifted up to 500 nm which is at lower energy than most background fluorescence signals from small chemical compounds.

Conclusion

1. Fluorescence anisotropylpolarization allows to monitor complex formation with high sensitivity. Based on the photophysical relation between fluorescence anisotropy and rotational and translational diffusion it can be concluded that 11 and related AlDA dye derivatives are suitable tracers in single-molecule specroscopy as well.

2. With avidin-biotin as model-system a tryptophan to 11 energy transfer of 70% relative to free avidin plus 11 was detected at 480 nm as efficient signal for complex formnation.

3. 70–80% reduction of fluorescence intensity of 11 which can comprise FRET, ground-state quenching of indazole and excited state quenching of the avidin label BODIPY-FL provides a third possibility for monitoring the protein-ligand complex between 440 and 500 nm.

EXAMPLE 3A

Detection of binding of AlDA-biotin conjugate 4-[1-[4-carbamoylphenyl]-1H-indazol-3yl]-benzoic acid 3-(biotinoylamino]-propyl amide (8) to avidin (a) Excitation and emission spectra of 8 and avidin showing the overlap between tryptophan emission and excitation spectra of 8 are presented in FIG. 2*c*. Wheras 11 has a very broad fluorescence emission band with about 50% of emission intensity at 500 nm (FIG. 2*b*) the fluorescence emission spectrum of 8 with the biotin linked to the indazole position 3 lacks the broad transition of 11 with a maximum at 450 nm, resulting in a much narrower spectrum. FIG. 2*f* and FIG. 2*i* show the spectral overlap integral between donor (the AlDA fluorescent molecule) and acceptor, Lucifer Yellow and BODIPY FL labels, respectively, in avidin. The different overlap integral for fluorescence emission of 11 and 8, respectively, and BODIPY absorption allows a qualitative estimation of the relative oriantation factor involved in the energy transfer process. It therefore remains a sole question of distance and non-radiative depopulation terms, whether efficient energy transfer will take place or not.

(b) Fluorescence Resonance Energy Transfer experiments with 11 as donor or acceptor.

AlDA conjugate 8 as acceptor (FIG. 3*b*)

The difference spectra $[|(8^{(free)})+|(avidin_{(free)})|]-|(8-avidin_{complex})$ (FIG. 3*b*, curve 5). Linking the biotin to position 3 in the indazole molecule in 8 (from position 1 in 11) not only changes the fluorescence spectra, but also the tryptophan to indazole FRET characteristics: indicated by 26% increase in indazole fluorescence emission (instead of quenching) an enhanced energy transfer to tryptophan (120%) is superimposed by a strong increase in indazole quantum yield in the avidin environment.

AlDA conjugate 8 as donor:(FIG. 3*d*)

Although the overlap integral between the indazole emission and the BODIPY-FL absorption spectrum is smaller for 8 than for 11, more sensitization of acceptor fluorescence occurs in the 8-avidin-BODIPY complex resulting in 48% fluoresence energy transfer and 93.5% indazole donor quenching. This effect can be caused by a higher donor quantum yield or a prefered relative orientation of the donor emission and acceptor absorption dipoles in 8.

Conclusions

With both molecular geometries, the indazole tracer linked via position 1 (11) and position 3 (8), binding of BODIPY-FL labelled avidin causes a 70–90% quenching of the indazole emission. This reduction in signal intensity can be caused by ground state quenching of the indazole or FRET to the BODIPY labels in avidin with concurrent non-radiative depopulation of the excited state. Besides of the donor quenching signal the acceptor sensitization will provide a selective interaction signal of AlDA conjugates with target macromolecules labelled with conventiuonal dyes fluorescing in >500 nm with FRET efficiencis of 40% and higher.

C. Binding of AlDA conjugate 8 to avidin-BODIPY detected by rotational diffusion and energy transfer: Energy transfer between the indazole moiety in 8 and the 3.3 BODIPY-FL lables on avidin by time-resolved fluorescence spectroscopy.

AlDA conjugate 8 exhibits fast fluorescence depolarisation in aqueous solution (PBS/5% DMSO), common to chromophores attached to a small molecule. Binding of avidin (unlabelled) leads to a slower depolarisation of 8 due to the decreased rotational diffusion of the complex. Binding of avidin labelled with BODIPY-FL to 8 creates a further depolarisation mode for the indazole fluorescence: Fluorescence resonance energy transfer between the indazole moiety of 8 and the BODIPY-FL labels. Therefore, although 8 binds to avidin via biotin, the rotational diffusion of the 8 bound to avidin-BODIPY monitored at the indazole emission wavelength is quickly depolarised, like in the unbound form. When the 8 -avidin BODIPY-FL complex is monitored at 550 nm (BODIPY emission wavelength), the rotational diffusion measured by the fluorescence anisotropy decay is as just a little bit slower than in the uncomplexed avidin-BODIPY construct.

Conclusion: The interaction between fluorescenctly labelled target macromolecules and AlDA conjugates can also be detected in the time-resolved set-up for fluorescence measurements by either monitoring changes in fluorescence lifetimes, rotational correlation times, or rotational or translational diffusion times in single molecule spectroscopy.

Part B: Chemical

General $^1$H-NMR spectra are recorded with a Bruker WC-250 or AMX-500 spectrometer; chemical shifts are given in ppm ( ä) relative to Me$_4$Si as internal standard. J values are given in hertz and are based upon first order spectral interpretation. Elemental analyses are performed by the Analytical Department, Novartis Basle, Switzerland and are within ±0.4% of the theoretical value unless otherwise stated. ESI-MS spectra are obtained on a Finnigan-SSQ 7000, and Cl-MS spectra on a Finnigan-TSQ 700. Melting points are determined with a Thermovar microscope (Reichert-Jung) and are uncorrected. Analytical thin layer chromatography (TLC): Merck precoated silica gel 60 F254 plates; detection: (a) λ=254 nm, (b) λ=366 nm, (c) staining with MOSTAIN (5% (NH$_4$)$_6$Mo$_7$O$_{24}$×4 H$_2$O, 0.1% Ce(SO$_4$)$_2$ in 10% H$_2$SO$_4$) or (d) staining with Ninhydrin (sat. soln. in ethanol) and subsequent heating on a hot plate. Medium pressure chromatography (MPLC): silica gel Merck 60 (40–63 μm). Reagents and solvents are purchased in analytical or the best available commercial quality and used without further purification unless otherwise stated. Evaporations are carried out in vacuo with a rotary evaporator; drying at high vacuum (HV) is performed under an oil pump vacuum better than 0.1 mbar.

Abbreviations

BOP (Benzotriazol-1-yloxy)-tris-(dimethylamino)-phosphonium hexafluorophosphate (Castro's Reagent)); Cl (Chemical Ionization); dec. (decomposition); DCM (DichloromethaneDIC (Diisopropylcarbodiimide); DIEA (Diisopropyl ethyl amine (H unig's base)); DMA (N,N-Dimethylacetamide); DMF (Dimethylformamide); DMEU (N,N'-Dimethylethylenurea); DMPU (N,N'-Dimethylpropylenurea); DMSO (Dimethylsulfoxide); ESI (Electrospray Ionization); Fmoc (9-Fluorenylmethoxycarbonyl); HOBt (1-Hydroxybenzotriazole); HV (High vacuum); m.p. (Melting point); MS (Mass spectrum); n.d. (not determined); RT (Room temperature);TEA (Triethylamine); TEM (Triethylammoniumacetate); TFA (Trifluoro acetic acid) ;THF (Tetrahydrofuran); TSTU (O-(N-Succinimidyl)-N,N, N',N'-tetramethyluronium tetrafluoroborate).

Synthetic Procedures

EXAMPLE 1B (a) General procedures for the synthesis of functionalized 1,3-Diaryl-1H-indazoles (4a–j) as illustrated in Scheme 1:

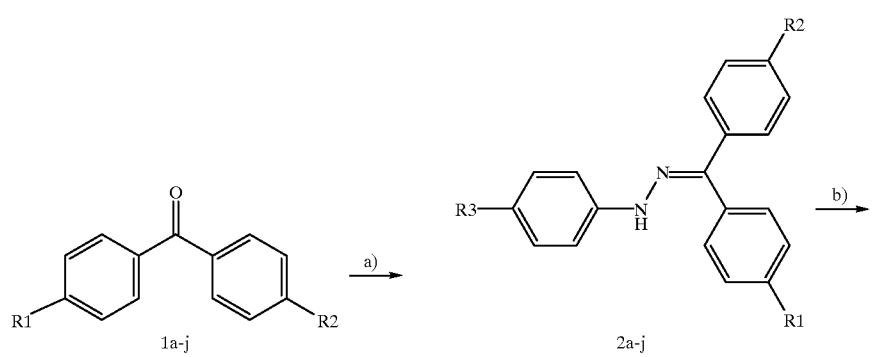

Scheme 1

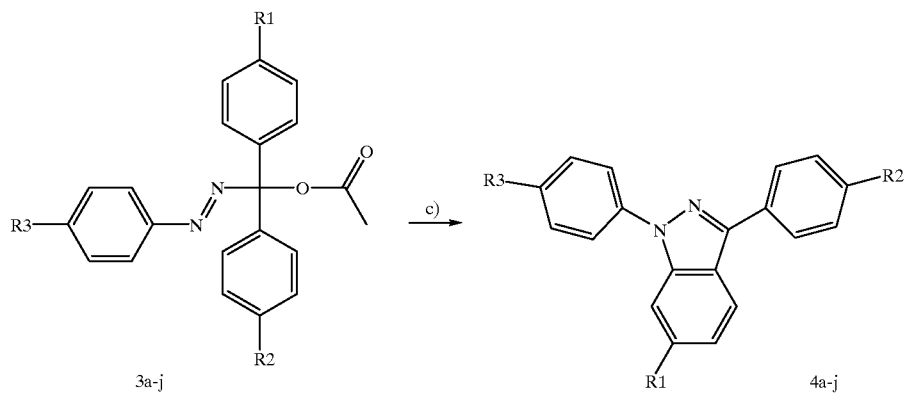

Conditions: (a) 4-Hydrazino-benzoic acid or 4-nitro-phenylhydrazine, MeOH, reflux, 50 h. (b) lead-tetraacetate, DCM, RT, 30–60 min. (c) DCM, boron-trifluoride etherate, 0° C., 20 min, RT, 30 min.

| 1-4 | a | b | c | d | e | f | g | h | i | j |
|---|---|---|---|---|---|---|---|---|---|---|
| R1 | H | H | H | H | H | H | Cl | MeO | H | $CH_3$ |
| R2 | H | $CO_2H$ | $CONH_2$ | $CO_2CH_3$ | $CO_2$allyl | $NO_2$ | Cl | MeO | $CO_2H$ | $NO_2$ |
| R3 | $CO_2H$ | $CO_2H$ | $CO_2H$ | $CO_2H$ | $CO_2H$ | $CO_2H$ | $CO_2H$ | $CO_2H$ | $NO_2$ | $CO_2H$ |

Synthesis of Arylhydrazones (2a–j) from Diarylketones (1a–j) as illustrated in Scheme 1. A suspension of the diarylketone (1a–j; 10 mmol) and the arylhydrazine (11 mmol) in methanol (50 mL) is refluxed for 50 h. Upon heating a clear solution is obtained. During the course of the reaction a crystalline precipitate is formed. After cooling in an ice bath the crystalline product (2a–j) is collected by filtration, washed twice with cold methanol and several times with diethylether. The crystals of 2a–j are kept overnight in a drying oven at 70° C. Unsymmetrically substituted diarylketones (1b–f, 1i–j) yield mixtures of E/Z-isomers (2b–f; 2i–j), which are introduced in the next reaction step without separation.

Yields and analytical data of 2a–j:

solution of lead tetraacetate (10 mmol) in dichloromethane (10 mL) is added at room temperature. The homogeneous reaction mixture is stirred for 30–60 min. The completion of the reaction is monitored by thin layer chromatography. A suspension of sodium oxalate (1 g in water) is added to the orange-yellow solution. After 15 min of vigorously stirring the entire mixture is filtered. The aqueous layer is discarded. The organic layer is extensively washed with water and evaporated under reduced pressure. The remaining orange oil is dissolved in ethyl acetate. The organic phase is washed again with several portions of water, dried over $MgSO_4$ and evaporated to dryness under reduced pressure. The remaining orange foam of 3a–j is further dried at room temperature in vacuo overnight. 3a–j are homogeneous as is indicated by

| 2 | | | | | | | | | | |
|---|---|---|---|---|---|---|---|---|---|---|
| | a | b | c | d | e | f | g | h | i | j |
| Yield [%] | 77 | 80 | 79 | 83 | 92 | 87 | 66 | 78 | 99 | 99 |
| m.p. [° C.] | 249–251 | 40:60* | 46:54* | 32:68* | 41:59* | 33:67* | 271–273 | 255–257 | 50:50* | 34:66* |
| $[MH]^+$ | 317 | 315 | 360 | 375 | 401 | 360 | 384 | 377 | 362 | 376 |
| $[M - H]^-$ | | —$CO_2H$ | | | | | | | | |

*ratio of E/Z-isomers (not assigned); $^1H/^{13}C$-NMR spectra; in agreement with the structures of 2a–j.

Synthesis of Acetic Acid 1,1-diaryl-1-arylazomethyl Esters (3a–j) as illustrated in Scheme 1. An arylhydrazone of 2a–j (10 mmol) is dissolved in dichloromethane (50 mL; complete solution can be obtained by addition of 10% acetic acid in case of low solubility of the starting material). A thin layer chromatography and are introduced in the next reaction step without further purification.

Yields and analytical data of 3a–j:

| 3 | | | | | | | | | | |
|---|---|---|---|---|---|---|---|---|---|---|
| | a | b | c | d | e | f | g | h | i | j |
| Yield-% | 88 | 93 | 93 | 97 | 99 | 99 | 99 | 99 | 90 | 99 |
| $[MH]^+$ | 271 | 359 | 358 | 373 | 399 | 418 | 441 | 375 | 360 | 374 |
| $[M - H]^-$ | (—OAc) | | | | (—OAc) | (—OAc) | | (—OAc) | (—OAc) | (—OAc) |

$^1H/^{13}C$-NMR spectra; in agreement with the structures of 3a–j.

Synthesis of 1,3-diaryl-1H-indazoles (4a–j) as illustrated in Scheme 1. An acetic acid 1,1-diaryl-1-arylazomethyl ester of 3a–j (10 mmol) is dissolved in dichloromethane (50 mL). The solution is cooled to 0° C. in an ice bath. Boron trifluoride etherate (13 mmol) is added under stirring within 5 min. The addition of boron trifluoride etherate results in instantaneous formation of a precipitate. The reaction mixture is stirred at 0° C. for 20 min and at room temperature for additional 30 min. The crystalline precipitate is collected by vacuum filtration. The crystals are washed twice with cold methanol and three times with diethylether. The 1,3-diaryl-1H-indazoles 4a–j are dried under reduced pressure in a drying oven at 70° C. Thin layer chromatography indicates homogeneity of 4a–j (recrystallization can be achieved from hot dimethylformamide, either pure or upon addition of methanol).

Yields and analytical data of 4a–j:

130.6; 131.2; 131.6; 136.8; 140.3; 143.3; 145.5; 167.3 ($\underline{C}$OOH); 167.6 ($\underline{C}$OOH).

4c: $^1$H-NMR (DMSO-$d_6$): 7.42 (ddd, 1H); 7.45 (broad, 1H, CONH); 7.62 (ddd, 1H); 8.02–8.06 (m, 3H); 8.08–8.10 (m, 2H); 8.12 (broad, 1H, CONH); 8.15–8.19 (m, 4H); 8.22–8.25 (dd, 1H); 12.5 (broad, 1H, COO$\underline{H}$). $^{13}$C-NMR (DMSO-$d_6$): 111.8; 122.0; 123.2; 123.6; 127.5; 128.7; 128.9; 131.4; 134.6; 135.2; 140.1; 143.2; 145.6; 167.1 ($\underline{C}$ONH$_2$); 167.9 ($\underline{C}$OOH).

4d: $^1$H-NMR (DMSO-$d_6$): 3.85 (s, 3H); 7.43 (t, 1H); 7.62 (t, 1H); 8.00–8.24 (m, 10H). $^{13}$C-NMR (DMSO-$d_6$): 52.3 (OCH$_3$); 111.5; 121.5; 121.8; 122.8; 123.4; 127.5; 128.3; 128.6; 129.4; 129.9; 131.0; 136.7; 139.7; 142.7; 144.7; 166.0; 166.7.

4e: $^1$H-NMR (DMSO-$d_6$): 4.84–4.86 (m, 2H); 5.29–5.32 (m; 1H); 5.42–5.46 (m, 1H); 6.05–6.12 (m, 1H); 7.41–7.44 (m, 3H); 8.07–8.19 (m; 4H); 8.21–8.24 (m, 3H). $^{13}$C-NMR

| | \multicolumn{10}{c}{4} | | | | | | | | | |
|---|---|---|---|---|---|---|---|---|---|---|
| | a | b | c | d | e | f | g | h | i | j |
| Yield [%] | 72 | 92 | 91 | 93 | 99 | 64 | 78 | 33 | 47 | 82 |
| m.p. [° C.] | 266–268 | 320 (dec.) | 322–323 | 313–314.5 | 238–240 | 306–307 | 341–342 | 243–246 | 273–275 | 355–360 |
| [MH]$^+$ [M – h]$^+$ | 315 | 359 | 358 | 373 | 399 | 359 | 382 | 375 | 360 | n.d. |

(b) Synthesis of 1,3-Diaryl5-nitro-1H-indazoles (4k, 4l)

4-[3-(4-carboxy-phenyl)-5-nitro-1H-indazol-1-yl-benzoic Acid (4k). Nitric acid (65%, 4 mL) is cooled to 0° C. in an ice bath and sulfuric acid (95%, 4 mL) is added. 1,3-Bis-(4-carboxy phenyl)-1H-indazole (4b) (300 mg, 0.835 mmol) is added at 0° C. under stirring. Cooling and stirring is continued for 10 min. The mixture is poured into ice-water (150 mL) and pH is adjusted to 4–5 by addition of 2N-NaOH. The crystals are collected by filtration, washed with brine until the filtrate was close to neutral. The crystals are dried for 2 h at 90° C. and recrystallized from dimethylformamide/methanol. The product is collected by filtration and dried at 120° C. under reduced pressure yielding 153 mg (45 %) of 4k: m.p. 348–350° C.

4-[3-(4-carbamoyl-phenyl)-5-nitro-1H-indazol-1-yl]-benzoic Acid (4l). Nitric acid (65%, 4 mL) is cooled to 0° C. in an ice bath and sulfuric acid (95%, 4 mL) is added. 4-[3-(4-carbamoyl-phenyl)-1H-indazol-1-yl]-benzoic acid (4c) (300 mg, 0.84 mmol) is added at 0° C. under stirring. Cooling and stirring is continued for 15 min. The mixture is poured into ice-water (150 mL). The precipitate is collected by centrifugation, washed with brine until the filtrate was close to neutral. The crystals are dried for 30 min at 120° C. and recrystallized from dimethylformamide/methanol. The product is collected by filtration and dried at 120° C. under reduced pressure yielding 211 mg (62%) of 4I: m.p. 320–322° C.

NMR spectral data of 4a–I

4a: $^1$H-NMR (DMSO-$d_6$): 7.36–7.47 (m, 1H); 7.47–7.50 (m, 1H); 7.54–7.59 (m, 3H); 7.99–8.02 (m, 3H); 8.03–8.06 (m, 2H); 8.14–8.18 (m, 3H). $^{13}$C-NMR (DMSO-$d_6$): 111.4; 121.5; 121.7; 123.0; 123.1; 127.6; 128.2; 128.4; 128.9; 129.2; 131.1; 132.3; 139.7; 143.1; 146.2; 166.8 (COOH).

4b: $^1$H-NMR (DMSO-$d_6$): 7.40 (ddd, 1H); 7.60 (ddd, 1H); 7.95–8.25 (m, 12H); 13.0 (broad, 2H). $^{13}$C-NMR (DMSO-$d_6$): 112.0; 122.1; 122.3; 123.4; 123.9; 127.9; 128.8; 129.2; (DMSO-$d_6$): 65.4; 111.6; 118.2; 121.7; 121.9; 122.9; 123.5; 127.7; 128.4; 128.8; 129.5; 130.1; 131.1; 132.8; 136.9; 139.9; 142.9; 144.8; 165.3 ($\underline{C}$O—O—allyl); 166.8 ($\underline{C}$OOH). Microanalysis: ($C_{24}H_{18}N_2O_4$) calculated, C 72.35, H 4.55, N 7.03; found, C 72.13, H 4.60, N 7.02.

4f $^1$H-NMR (DMSO-$d_6$): 8.6–7.2 (m; aromat. H). $^{13}$C-NMR (DMSO-$d_6$): 112.12; 121.9; 122.5; 123.2; 124.2; 124.8; 128.7; 128.9; 129.4; 131.5; 140.2; 140.4; 143.1; 143.3; 147.6; 167.2 ($\underline{C}$O$_2$H).

4g: $^1$H-NMR (DMSO-$d_6$; 330° K.): 8.15 (m, 3H), 8.05 (m, 3H), 7.98 (m, 2H), 7.60 (m, 2H), 7.40 (ddd, 1H). $^{13}$C-NMR (DMSO-$d_6$, 330° K.) 111.8; 122.3; 122.7; 123.9; 124.5; 130; 131.4; 131.8; 134.3; 134.6; 141.1; 143.2; 145.9; 167.5 ($\underline{C}$O$_2$H).

4h: $^1$H-NMR (DMSO-$d_6$): 3.86 (s, 3H, OCH$_3$); 3.92 (s, 3H, OCH$_3$); 7.00 (dd; 1H); 7.10 (m, 2H); 7.35 (d, 1H); 7.95–8.05 (m, 5H); 8.15–8.22 (m, 2H); 12.0 (broad, 1H, COO$\underline{H}$). $^{13}$C-NMR (DMSO-d6): 55.2 (OCH$_3$); 55.6 (OCH$_3$); 92.8; 113.9; 114.4; 117.3; 121.3; 122.4; 124.7; 127.9; 128.6; 130.9; 140.9; 143.1; 145.8; 159.7; 160.0; 166.7 ($\underline{C}$OOH).

4i: $^1$H-NMR (DMSO-$d_6$): 7.5 (ddd, 1H); 7.7 (ddd, 1H); 8.1–8.3 (m, 8H); 8.45 (m, 2H). $^{13}$C-NMR (DMSO-$d_6$) :112.0; 122.2; 122.3 (2x); 123.6; 124.1; 125.8 (2x); 127.9 (2x); 129.1; 130.4 (2x); 131.3; 136.2; 140.1; 144.8; 145.1; 146.3; 167.4 ($\underline{C}$=O).

4j: $^1$H-NMR (DMSO-$d_6$): 2.54 (s, 3H); 7.30 (d, 1H); 7.83 (s, 1H); 8.01 (d, 2H); 8.14 (d, 1H); 8.18 (d, 2H); 8.33–8.40 (m, 4H); 12.8 (broad, COO$\underline{H}$).

4k: $^1$H-NMR (DMSO-$d_6$): 7.97 (2H); 8.05 - 8.20 (m, 7H); 8.38 (dd, 1H); 8.93 (d, 1H). 11.5 (broad, 2H). $^{13}$C-NMR (DMSO-$d_6$): 112.8; 119.2;122.3; 122.8; 123.2; 128.0; 130.1; 130.6; 131.4; 131.7; 135.1; 141.9; 142.1; 143.6; 147.4; 166.9 ($\underline{C}$OOH); 167.3 ($\underline{C}$OOH).

4l: $^1$H-NMR (DMSO-$d_6$): 7.52 (broad, NH.); 8.0 (m, 2H); 8.3–8.05 (m, 7H); 8.35 (dd, 1H); 8.94 (d, 1H); 11.2 (broad, COO<u>H</u>). $^{13}$C-NMR (DMSO-d$_6$): 113.0; 119.6; 122.7; 123.1; 123.5; 128.1; 129.1; 130.3; 131.7; 134.0; 135.6; 142.2; 142.5; 143.9; 148.1; 167.2; 168.1.

EXAMPLE 2B (a) Synthesis of 4-{3-{4-[(3-Aminopropyl)-aminocarbonyl]-phenyl}-1H-indazol-1 yl}-benzoic Acid (5) as illustrated in Scheme 2.

Scheme 2

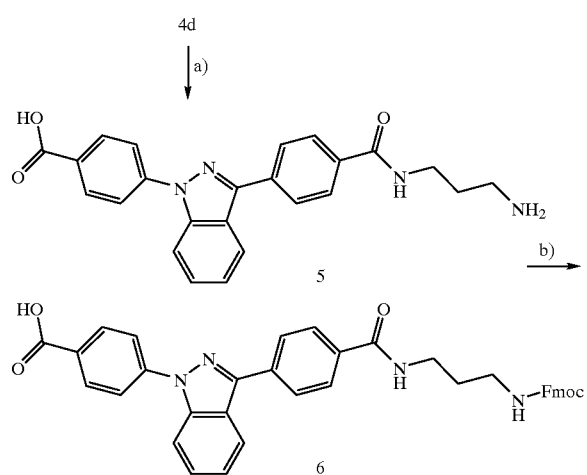

Conditions:
(a) 1,3-diaminopropane (neat), 90° C., 4H.
(b) K$_2$CO$_3$, water, 1, 4-dioxane, Fmoc-Cl, 0° C., 10 min., RT, 12h.

1,3-diamino-propane (80 mL) is added to 4d (10.0 g, 26.85 mmol). The heterogeneous reaction mixture is heated to 90° C. under stirring. 4d dissolves once the solvent is at reaction temperature, and the solution is then left to react for 4h. The 1,3-diamino-propane is distilled off under reduced pressure leaving a viscous oil behind. The crude product is diluted with methanol (200 mL) and heated to reflux. Before the methanol reaches boiling temperature, crystalline product starts to precipitate. The suspension is refluxed for 10 min and then cooled to room temperature. The crystals are collected by vacuum filtration. The colourless crystals are washed with a portion of glacial methanol and then with several portions of diethyl ether. The product is dried in a drying oven under reduced pressure at 120° C., yielding 9.86 g (89 %) of 5: mp 285–288° C. (depending on the heating rate; dec.); $^1$H-NMR (DMSO-d$_6$): 1.85–2.05 (m, 2H); 2.90–3.05 (m, 2H); 3.35–3.55 (m, 2H); 7.32 (t, 1H); 7.51 (t, 1H); 7.75–8.30 (m, 1OH); 9.20 (broad, t, 1H, CON<u>H</u>); $^{13}$C-NMR (DMSO-d$_6$): 27.5; 36.2; 36.4; 111.2; 121.2; 121.4; 122.4; 122.8; 126.9; 127.8; 128.0; 130.4; 134.0; 135.0; 137.0; 139.7; 140.2; 143.9; 144.2; 165.8; MS: e/m 415 (MH$^+$).

(b) Synthesis of 4-{3-{4-[N-3-[(9H-Fluoren-9-yl)-methyloxycarbonylamino]-propyl]-aminocarbonyl}-phenyl-1H-indazol-1-yl} benzoic Acid (6) as illustrated in Scheme 2

Potassium carbonate (2.67 g; 15.45 mmol) is added to a suspension of the amino acid 5 (3.20 g; 7.73 mmol) in water (60 mL) and 1,4-dioxane (35 mL). The mixture is stirred for 5 min and cooled to 0° C. in an ice bath. Fmoc-chloride (2.20 g; 8.5 mmol) in 1,4-dioxane (35 mL) is added dropwise within 10 min. Cooling is removed and stirring continued at room temperature for 12 h. A bulky precipitate is formed. The aqueous suspension is extracted with diethyl ether. The pH is adjusted to 1 with dilute HCl and then further diluted with brine (100 mL). The precipitate is collected by vacuum filtration and washed extensively with diethyl ether to achieve lumpy crystals. The product is dried for 24 h at 35° C. in a drying oven under reduced pressure, yielding 4.14 g (84%) of 6: mp 217–219.5 ° C (depending on the heating rate, dec.); $^1$H-NMR (DMSO-d$_6$): 1.68–1.77 (m, 2H); 3.05–3.12 (m, 2H), 3.25–3.35 (m, 2H); 4.22 (t, 1H, H-9 fluorenyl); 4.33 (d, 2H, OCH$_2$-9-fluorenyl); 7.27–7.35 (m, 3H), 7.37–7.46 (m, 3H); 7.63 (t, 1H); 7.70 (d, 2H, H-fluorenyl); 7.88 (d, 2H, H-fluorenyl); 8.01–8.08 (m, 5H); 8.15–8.20 (m, 4H); 8.24 (d, 1H); 8.58 (t, 1H, CON<u>H</u>); $^{13}$C-NMR (DMSO-d$_6$): 29.6; 37.2; 38.4; 47.0; 65.4; 111.6; 120.2; 120.3; 121.8; 123.0; 123.4; 125.2; 125.3; 127.2; 127.3; 127.8; 128.1; 128.4; 128.7; 131.2; 134.7; 134.8; 139.9; 140.9; 143.0; 144.1; 145.3; 156.3; 166.0; 166.9; MS: 635 (M-H)$^-$.

EXAMPLE 3B (a) Synthesis of 3'(+)-4-{3-[4-(3'-Biotinoylaminopropyl)-aminocarbonyl]phenyl-1H-indazol-1-yl}-benzoic acid Amide (8) as illustrated in Scheme 3. Scheme 3

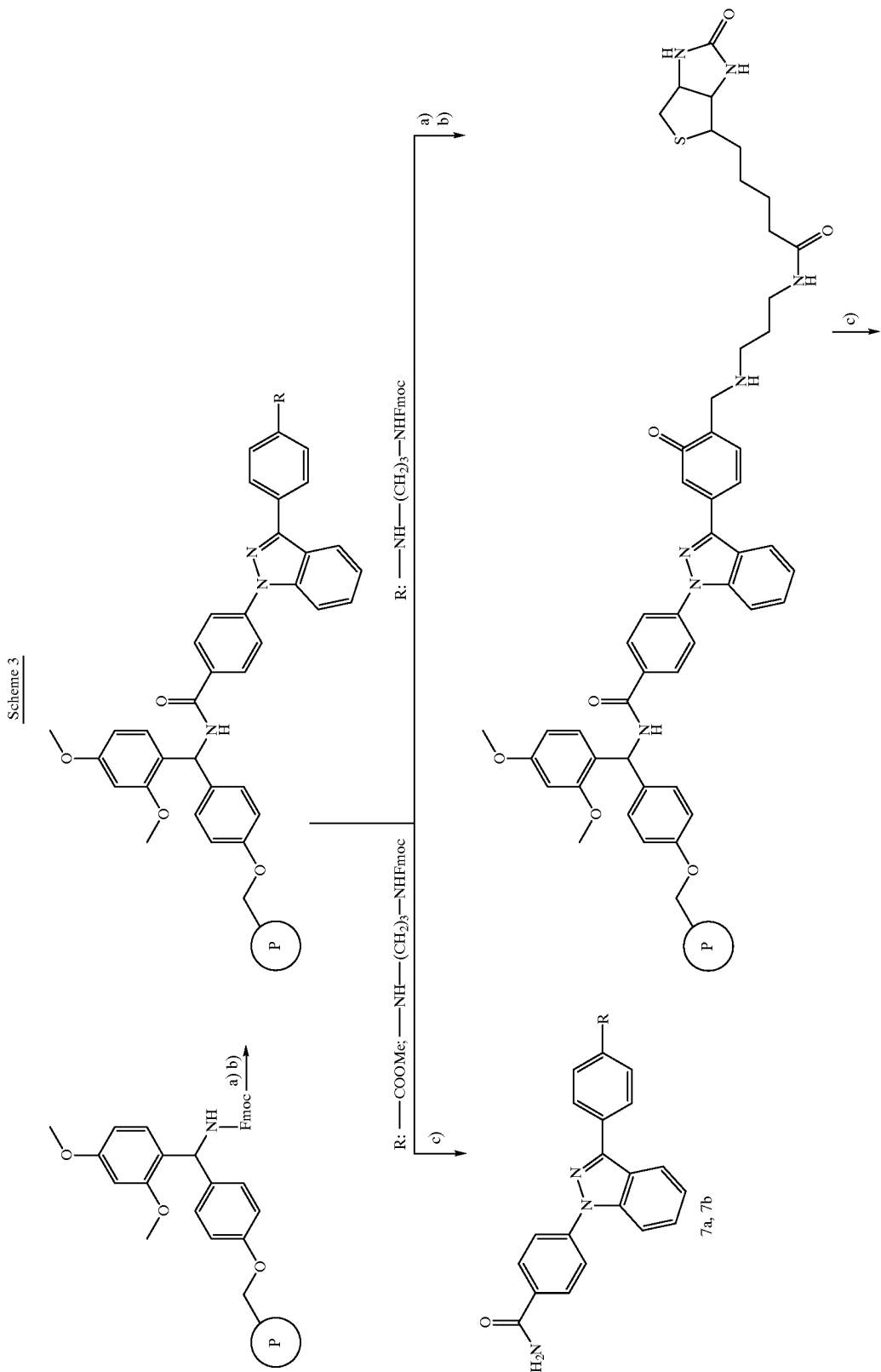

-continued
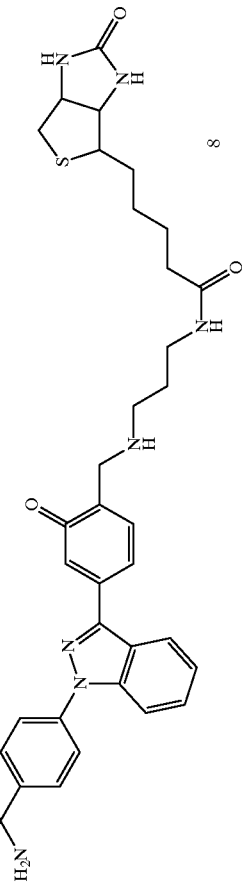
| | R |
|---|---|
| 7a | —COOMe |
| 7b | —NH—(CH$_2$)$_3$—NHFmoc |
Conditions:
(a) DCM/piperidine.
(b) 6 or 4d, DIC, HOBt, DMF.
(c) DCM/TFA.
(d) (+)-biotin, DIC, HOBt, DMF.

Rink amide resin (500 mg; 0.28 mmol) is shaken with piperidine (20%) in dichloromethane (10 mL) at room temperature for 1 h. The resin is washed with portions of dichloromethane, methanol and finally dichloromethane, until a sample of the latest filtrate shows no presence of cleaved protecting group. The resin is shaken in a solution prepared from 6 (0.56 mmol), 1-hydroxybenzotriazole (1.68 mmol), N,N'-diisopropyl carbodiimide (2.24 mmol) and dimethylformamide (35 mL) overnight at room temperature. The resin is washed thoroughly with several portions of dimethylformamide, then methanol, and finally dichloromethane. The washing continues until the latest filtrate is free of fluorescence. Solvents are evaporated under reduced pressure at room temperature. The Fmoc protecting group of resin bound 6 is removed as described above for deprotection of the Rink amide resin. To a solution of (+)-biotin (0.84 mmol) and 1-hydroxybenzotriazole (2.52 mmol) in dimethylformamide (40 mL) is added N,N'-diisopropyl carbodiimide (5.04 mmol). The solution is left at room temperature for 1 h and then transferred to the resin. The reaction vessel is gently agitated by circular motion for 24 h. Solvents are removed by vacuum filtration. The resin is washed thoroughly with portions of dimethylformamide, methanol, and finally with dichloromethane. Crude product (8) is cleaved from the solid support by treatment of the resin with a 1:1 mixture of dichloromethane and trifluoroacetic acid (15 mL) for 2 min. The solution is collected by vacuum filtration. The resin is further extracted with three portions of dichloromethane. The solvents are removed under reduced pressure, yielding 8 as viscous oil in high purity as indicated by $^1$H-NMR. Triturating with ether induces crystallization. Recrystallization from a mixture of dimethylsulfoxide, methanol, and diethyl ether yields 60 mg (33%) of 8: mp 222–225° C.; $^1$H-NMR (DMSO-$d_6$): 1.25–1.66 (m, 6H, biotin); 1.67–1.72 (m, 2H, NHCH$_2$C$\underline{H}_2$CH$_2$NH); 2.09 (t, 2H, COC$\underline{H}$2); 2.56, 2.58, 2.79, 2.80, 2.81, 2.82 (2H, C$\underline{H}_2$S, AB-part of ABX); 3.08–3.10 (m, 1H, C$\underline{H}$S-biotin); 3.11–3.15 (m, 2H, NC$\underline{H}_2$); 3.30–3.34 (m, 2H, NC$\underline{H}_2$); 4.11–4.14 (m, 1H, CH-biotin); 4.28–4.30 (m, 1H, CH-biotin, X-part of ABX); 6.34 (s, broad, 1H, N$\underline{H}$CONH); 6.42 (s, broad, 1H, NHCON$\underline{H}$); 7.44 (ddd,1H); 7.47 (s, broad, 1H of CON$\underline{H}_2$); 7.61 (ddd, 1H); 7.84 (t, 1H, N$\underline{H}$CO); 7.97–8.06 (m, 5H); 8.12 (s, broad, 1H of CON$\underline{H}_2$); 8.13–8.26 (m, 5H); 8.59 (t, 1H, N$\underline{H}$CO). MS: e/m 640 (MH)$^+$. $^{13}$C-NMR (DMSO-$d_6$): 25.5; 28.2; 28.4; 29.5; 35.5; 36.5; 37.3; 55.6; 56.2; 59.4; 61.2; 111.5; 121.9; 122.8; 123.2; 127.3; 128.1; 129.3; 132.4; 134.6; 135.0; 139.9; 141.7; 145.0; 162.9; 165.9; 167.3; 172.3. Microanalysis: (C$_{34}$H$_{37}$N$_7$O$_4$S$_1$xH$_2$O) calculated, C 62.08, H 5.98, N 14.91, S 4.87; found C 62.19, H 5.82, N 14.78, S 4.67.

(b) Synthesis of 4-[3-4-Methoxycarbonyl-phenyl)-1H-indazol-1-yl]-benzoic Acid Amide (7a) as illustrated in Scheme 3

Rink amide resin (1.786 g; 1.00 mmol) is deprotected as described previously. The deprotected resin is shaken in a solution prepared from 4d (745 mg; 2.00 mmol), 1-hydroxybenzotriazole (810 mg, 6.00 mmol), N,N'-diisopropyl carbodiimide (1.010 g, 8.00 mmol) and dimethylformamide (100 mL) overnight at room temperature. The resin is washed thoroughly with several portions of dimethylformamide, then methanol, and finally dichloromethane. The washing continues until the latest filtrate is free of fluorescence. Solvents are evaporated under reduced pressure at room temperature. An aliquot of product (7a) is cleaved from the solid support (200 mg) by treatment of the resin with a 2:1 mixture of dichloromethane and trifuoroacetic acid (10 mL) for 10 min. The solution is collected by vacuum filtration. The resin is further extracted with three portions of dichloromethane, followed by two portions of dimethylformamide. Removal of the solvents under reduced pressure and drying overnight in a desiccator provides 34.0 mg (98%) of 7a: mp 267–269° C.; homogeneous by thin layer chromatography: $R_f$=0.68; dichloromethane: methanol=9:1); $^1$H-NMR (DMSO-$d_6$): 3.92 (s, 3H, OC$\underline{H}_3$); 7.43 (ddd, 1H); 7.61 (ddd, 1H); 7.95–8.00 (m, 3H); 8.13–8.16 (m, 4H); 8.23–8.25 (m, 3H); CON$\underline{H}_2$ broad (not assignable); $^{13}$C-NMR (DMSO-$d_6$): 51.9 (COO$\underline{C}$H$_3$); 121.2; 121.6; 122.6; 123.0; 127.3; 127.9; 129.0; 129.4; 129.7; 132.5; 136.8; 139.9; 141.4; 144.4; 165.9 ($\underline{C}$ONH$_2$); 167.03 ($\underline{C}$OOCH$_3$).

(c) Synthesis of 4-{3-{4-{3-[(9H-Fluoren-9-yl)-methyloxycarbonylamino]-propyl}-aminocarbonyl}-phenyl-1H-indazol-1-yl} benzoic Acid Amide (7b) as illustrated in Scheme 3.

Rink amide resin (1.00 g; 0.56 mmol) is deprotected as described previously. The deprotected resin is shaken in a solution prepared from 6 (1.12 mmol), 1-hydroxybenzotriazole (3.36 mmol), N,N'-diisopropyl carbodiimide (4.48 mmol) and dimethylformamide (50 mL) overnight at room temperature. The resin is washed thoroughly with several portions of dimethylformamide, then methanol, and finally dichloromethane. The washing continues until the latest filtrate is free of fluorescence. Solvents are evaporated under reduced pressure at room temperature. An aliquot of product (7b) is cleaved from the solid support (51 mg) by treatment of the resin with a 2:1 mixture of dichloromethane and trifluoroacetic acid (3 mL) for 10 min. The solution is collected by vacuum filtration. The resin is further extracted with three portions of dichloromethane, followed by two portions of dimethylformamide. Removal of the solvents under reduced pressure provides 40.5 mg (88%) of 7b as an amorphous solid in high purity as indicated by $^1$H-NMR and thin layer chromatography ($R_f$= 0.64; dichloromethane: methanol=9.5: 0.5; +trace of acetic acid); $^1$H-NMR (DMSO-$d_6$): 1.71 (m, 2H, CONHCH$_2$C$\underline{H}_2$CH$_2$NHCOO); 3.09 (m, 2H, NHCH$_2$CH$_2$C$\underline{H}_2$NHCOO); 3.32 (m, 2H, CONHC$\underline{H}_2$CH$_2$CH$_2$NHCOO); 4.22 (distort. t, 1H, H-9 fluorenyl); 4.32 (distort. d, 2H, COOC$\underline{H}_2$-(9-fluorenyl); 7.30–7.35 (m, 2H, fluorenyl; 1H, —CONHCH$_2$CH$_2$CH$_2$N$\underline{H}$COO)); 7.40–7.44 (m, 2H, fluorenyl; 1H, indazole); 7.47 (s, broad, 1H of —CONH$_2$); 7.60–7.63 (ddd, 1H, indazole); 7.70 (d, 2H, fluorenyl); 7.88 (d, 2H, fluorenyl); 7.97–8.06 (m, 5H, indazole); 8.12 (s, broad, 1H of —CON$\underline{H}_2$); 8.13–8.25 (m, 3H, indazole); 8.58 (t, 1H, CON$\underline{H}$CH$_2$CH$_2$CH$_2$NHCOO).

EXAMPLE 4B (a) Synthesis of 4-13-(4-Allyloxycarbonyl-phenyl)-indazol-1-yl]-benzoic Acid 2,5-Dioxo-pyrrolidin-1-yl Ester (10) as illustrated in Scheme 4

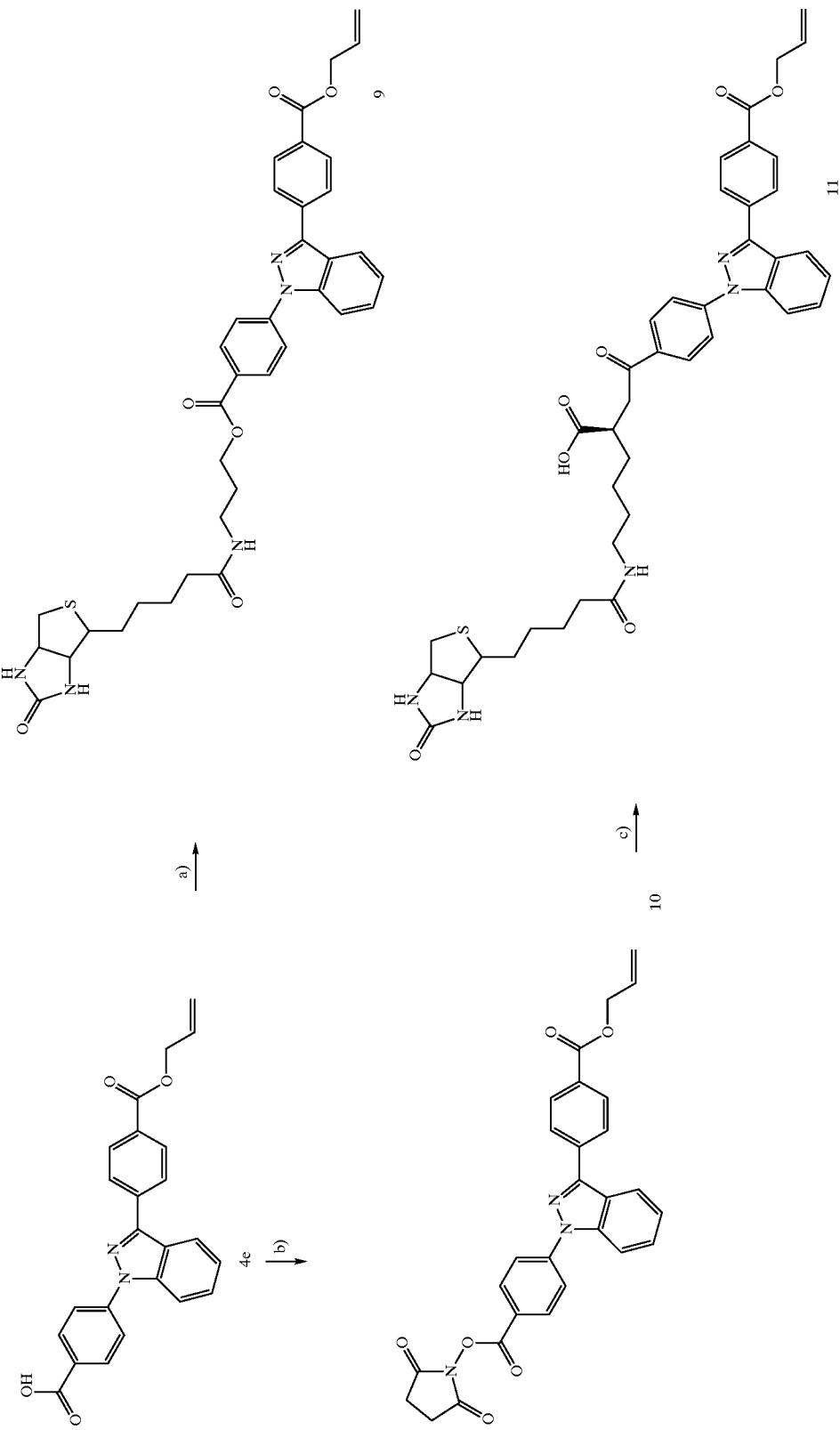

To a stirred solution of 4e (355 mg, 0.891 mmol) and N-hydroxy-succinimide (106 mg, 0.891 mmol) in dioxane (20 mL), diisopropylcarbodiimide (0.141 mL, 0.891 mmol) is slowly added via a syringe under an argon atrnosphere. The mixture is stirred for 72 h at room temperature and subsequently evaporated to dryness. The residue is redissolved in ethyl acetate (60 mL) and washed consecutively with $NH_4Cl_{sat.aq.}$, $NaCl_{sat.aq.}$, and water (10 mL each). The collected aqueous phases are extracted once with ethyl acetate (10 mL). Pooled organic phases are dried over $MgSO_4$ and evaporated to dryness. The resulting yellowish, amorphous solid is purified twice by MPLC (eluent of 1st chromatography: cyclohexane: ethyl acetate=2:1; eluent of 2nd chromatography: toluene: ethyl acetate=12:1) to give 370 mg (83%) of 10:mp 178° C.; homogeneous by thin layer chromatography: $R_f$=0.20 (cyclohexane : ethyl acetate=2:1). $^1$H-NMR (DMSO-$d_6$): 2.93 (s, 4H); 4.85–4.88 (m; 2H); 5.30–5.33 (m, 1H); 5.42–5.47 (m, 1H); 6.05–6.13 (m, 1H); 7.45–7.49 (t, 1H); 7.64–7.68 (t, 1H); 8.11–8.32 (m, 1OH). MS: m/e 496 (MH$^+$). Microanalysis: ($C_{28}H_{21}N_3O_6$) calculated, C 67.87, H 4.27, N 8.48; found, C 67.99, H 4.34, N 8.70.

(b) (5S)-4-{1-[4-(5-Carboxy-5-biotinoylamino)-pentylcarbamoyl)-phenyl]-1H-indazol-3-yl}-benzoic Acid Allyl Ester Triethylammonium salt (11) as illustrated in Scheme 4

To a stirred solution of ω-(+)-biotinoyl-(L)-lysine (50 mg, 0.134 mmol) and $NaHCO_3$ (23 mg, 0.268 mmol) in water (2 mL) 10 (100 mg, 0.201 mmol) is added. The suspension is diluted with dioxane/dimethylformamide (1/1, 4 mL) and stirred at room temperature under an atmosphere of argon for 6 d to result in a slightly turbid solution, which is further diluted with water (10 mL) and lyophilized to give a yellowish powder. The raw material is purified via preparative RP18-HPLC employing a linear 0.1M TEAA (pH 7.0)1CH3CN-gradient (90:10®0:90). Product-containing fractions are pooled, diluted with water and lyophilized to give 99 mg (86%) of 11 as a white powder (the purity of which is larger than 98%, as determined by analytical RP18-HPLC; UV/fluorescence detection): mp 45° C.;

$^1$H-NMR (DMSO-$d_6$): 1.00 (t, 9H, ($CH_3CH_2)_3NH^+$); 1.22–1.63 (m, 11H); 1.72–1.88 (m, 2H); 2.03 (t, 2H); 2.55 (d, 1H); 2.62 (q, 6H, ($CH_3CH_2)_3NH^+$); 2.77 (dxd, 1H); 3.00–3.07 (m, 2H); 4.07–4.10 (m, 1H); 4.25–4.30 (m, 2H, —O—$CH_2$—CH=$CH_2$); 5.30–5.33 (m,1H, =$CH_2$); 5.43–5.47 (m, 1H, =$CH_2$); 6.06–6.13 (m, 1H, —CH=$CH_2$); 6.32 (s, 1H, NH, biotin); 6.40 (s, 1H, NH, biotin); 7.45 (dxd, $J_1=J_2$, 1H); 7.63 (dxd, $J_1=J_2$, 1H); 7.76 (t, 1H, —CONH-($CH_2)_4$—, lysine); 7.99, 8.00 and 8.13, 8.14 (AA'BB', 4H); 8.02 (d, J=5.5, 1H); 8.17, 8.19 and 8.26, 8.28 (AA'BB', 4H); 8.27 (d, J=6.6, 1H); 8.44 (d, J=7.4, 1H, —NH—). $^{13}$C-NMR (DMSO-$d_6$): 10.8 (($CH_3CH_2)_3NH^+$); 23.3 ($CH_2$); 25.5 ($CH_2$); 28.2 ($CH_2$); 28.4 ($CH_2$); 29.2($CH_2$); 31.2 ($CH_2$); 35.4 ($CH_2$); 38.5 ($CH_2$); 45.6 (($CH_3CH_2)_3NH^+$); 53.7 ($CH$); 55.6 (CH); 59.3 (CH); 61.2 (CH); 65.4 (—O—CH2—); 111.6 (CH); 118.2 (=CH2); 121.6 (CH); 122.0 (CH); 122.8 (C-quart.); 123.4 (CH); 127.7 (CH); 128.4 (CH); 129.1 (CH); 129.4 (C-quart.); 130.2 (CH); 132.7 (C-quart.); 132.8 (CH); 137.1 (C-quart.); 140.0 (C-quart.); 141.5 (C-quart.); 144.5 (Cquart.); 162.9 (C=O); 165.2 (C=O); 165.3 (C=O); 172.0 (C=O); 174.2 (C=O). MS: m/e 753 (MH$^+$), 775 ([M+Na]$^+$). Microanalysis: ($C_{46}H_{59}N_7O_7S$ x 2.5 $H_2O$) calculated, C 61.45, H 7.18, N 10.90, S 3.56; found, C 61.64, H 6.35, N 10.76, S 3.14.

(c) 4-[3-(4-Allyloxycarbonylphenyl)-1H-indazol-1-yl]-benzoic Acid (5S) 3-(Biotinoylamino)-propyl Ester (9) as illustrated in Scheme 4

To a stirred solution of 4e (1070 mg, 2.677 mmol), BOP (1303 mg, 2.945 mmol) and DIEA (688 μL, 4.016 mmol) in DMPU (15 mL), a solution of (+)-biotin 3-hydroxypropyl amide (807 mg, 2.677 mmol) and 1,2,4-triazole (203 mg, 2.945 mmol) in DMPU (10 mL) is slowly injected through a septum at room temperature under an atmosphere of argon. The resulting yellow solution is further stirred under argon for 6 d and evaporated to dryness (HV, bath temperature: 75° C.). The resulting yellow oil is purified by MPLC (dichloromethane:methanol=20:1) to give a yellowish solid (1.258 g, 69%), which is further purified by recrystallization from acetonitrile-water (1:1) yielding 820 mg (45%) of 9: mp 154–157° C. (acetonitrile/water); homogeneous as indicated by thin layer chromatography: $R_f$=0.24 dichloromethane:methanol=15:1). $^1$H-NMR (DMSO-$d_6$): 1.25–1.38 (m, 2H, biotin); 1.42–1.57 (m, 3H, biotin); 1.58–1.63 (m, 1H, biotin); 1.88 (txt, J=5.6, 2H, —$OCH_2$—$CH_2$—$CH_2NH$—); 2.08 (t, 2H, —CO—$CH_2$—); 2.56 (d, 1H, biotin); 2.79 (dxd, 1H, biotin); 3.05–3.10 (m, 1H, biotin); 3.22–3.26 (m. 2H, —$OCH_2CH_2$—$CH_2$—NH—); 4.10–4.13 (m, 1H, biotin); 4.27–4.30 (m, 1H, biotin); 4.32 (t, 2H, —O—$CH_2$—$CH_2CH_2NH$—); 4.86–4.88 (m, 2H, —O—$CH_2$—CH=$CH_2$); 5.30–5.33 (m, 1H, =$CH_2$); 5.42–5.47 (m,1H, =$CH_2$); 6.05–6.13 (m, 1H, —CH=$CH_2$); 6.34 (s, 1H, NH, biotin); 6.41 (s, 1H, NH, biotin); 7.44 (t, 1H); 7.64 (t, 1H); 7.90 (t, 1H, NH-($CH_2)_3$—O—); 8.03–8.08 (m, 3H); 8.17–8,21 (m, 4H); 8.24–8.27 (m, 3H). $^{13}$C-NMR (DMSO-$d_6$): 25.5; 28.2; 28.4; 28.6; 35.4; 35.5; 40.0; 55.6; 59.4; 61.2; 62.9; 65.4; 111.6; 118.2; 121.7; 122.0; 123.0 (C-quart.); 123.6; 127.7; 127.8 (C-quart.); 128.5; 129.6 (C-quart.); 130.1; 131.0; 132.8; 136.9 (C-quart.); 139.9 (C-quart.); 143.2 (C-quart.); 145.0 (C-quart.); 162.9; 165.3; 172.3. MS: mie 682 (MH$^+$). Microanalysis: ($C_{37}H_{39}N_5O_6S$ x $H_2O$) calculated, C 63.50, H 5.90, N 10.01, S 4.57; found, C 64.00, H 5.73, N 10.42, S 4.24.

EXAMPLE 5B

Synthesis of 4-[3-(4-Aminocarbonyl-phenyl)-1H-indazol-1-yl)-benzoic Acid Amides (12 a–j) as illustrated in Scheme 5

Scheme 5

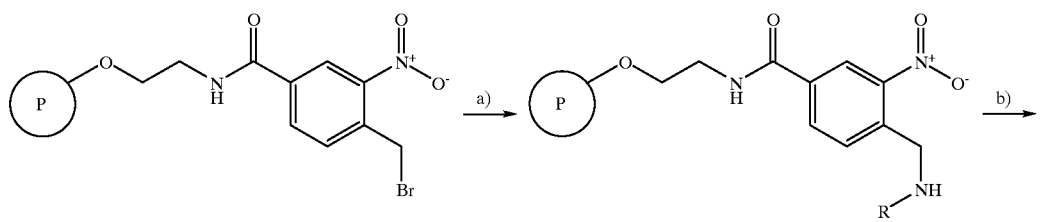

-continued

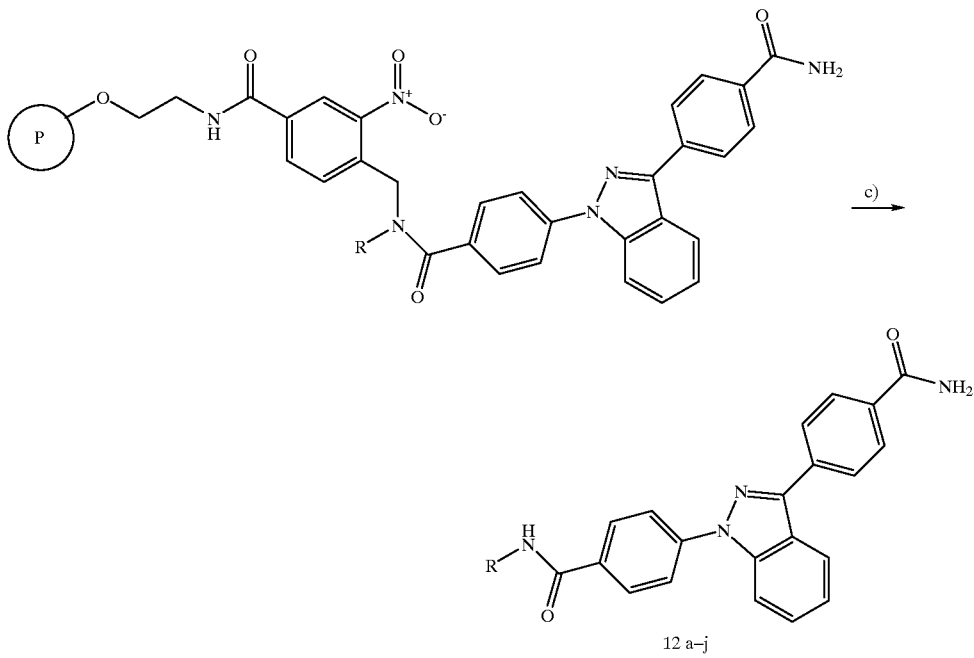

Conditions:
(a) amine (RNH2), THF, 24 h, RT.
(b) 4c, HOBT, DIC, DMF, 24 h, RT.
(c) DCM/MeOH, irradiation, 24 h (366 nm).

Aminoethyl-Tentagel resin (capacity: 0.29 mmol/g) is loaded with photolabile 4-bromomethyl-3-nitro benzoic acid linker by standard procedure. Portions of the resin (200 mg; load: 0.27 mmol/g) are reacted with different primary amines (a–j) (1.08 mmol in 5 mL of tetrahydrouran) for 24 h at room temperature. The resins are washed with several portions of tetrahydrofuran, methanol, finally with dichloromethane, and dried in a desiccator under reduced pressure. To a solution of 4c (579 mg, 1.62 mmol) and 1-hydroxybenzotriazole (657 mg, 4.86 mmol) in dimethylformamide (30 mL) is added N,N'-diisoprnpylcarbodiimide (1.23 g; 9.72 mmol). The reaction mixture is stirred for 30 min at room temperature. The stock solution is divided in ten aliquots (3 mL) which are added to the resins prepared. The resins are shaken at room temperature for 24 h. Reagent containing solutions are removed by vacuum filtration. The resins are washed with several portions of dimethylformamide, methanol, and finally with dichloromethane. The resins are transferred into glass vials and covered by dichloromethane (5 mL). Methanol is added to achieve isodense solutions. The vials are shaken under irradiation with an UV-lamp (366 nm) for 24 h. After this time the resins are removed by vacuum filtration and the solvents evaporated to dryness. The purity of the products (12 a–j) is analyzed by RP-HPLC, and the presence of the compounds 12 a–j is verified by mass spectrometry:

| 12 | R | Yield [%] HPLC [%] | MS (ESI) | 12 | R | Yield [%] HPLC [%] | MS (ESI) |
|---|---|---|---|---|---|---|---|
| a | 2-methoxybenzyl | 38 / 69 | 513 (M + Na)+ | f | $(CH_3)_2CH$ | 23 / 61 | 399 (MH)+ |
| b | 2-chlorobenzyl | 52 / 76 | 517 (M + Na)+ | g | $CH_3(CH_2)_4$ | 52 / 76 | 427 (MH)+ |
| c | 2-methylpyridyl | 32 / 64 | 470 (M + Na)+ | h | $(CH_3)_2CH(CH_2)_2$ | 42 / 89 | 449 (M + Na)+ |

-continued
| 12 | R | Yield [%] HPLC [%] | MS (ESI) | 12 | R | Yield [%] HPLC [%] | MS (ESI) |
|---|---|---|---|---|---|---|---|
| d | 3-pyridylmethyl | 31 / 58 | 470 (M + Na)+ | i | cyclohexylmethyl | 36 / 63 | 453 (MH)+ |
| e | 3,4-dimethoxyphenethyl | 65 / 77 | 521 (MH)+ | j | cyclopropylmethyl | 55 / 83 | 433 (M + Na)+ |
EXAMPLE 6B
Synthesis of 4-(3-{4-[3-(arylsulfonylamino)-propylcarbamoyl]-phenyl}-indazol-1-yl)-benzoic Acid Amides (13 a–d) as illustrated in Scheme 6
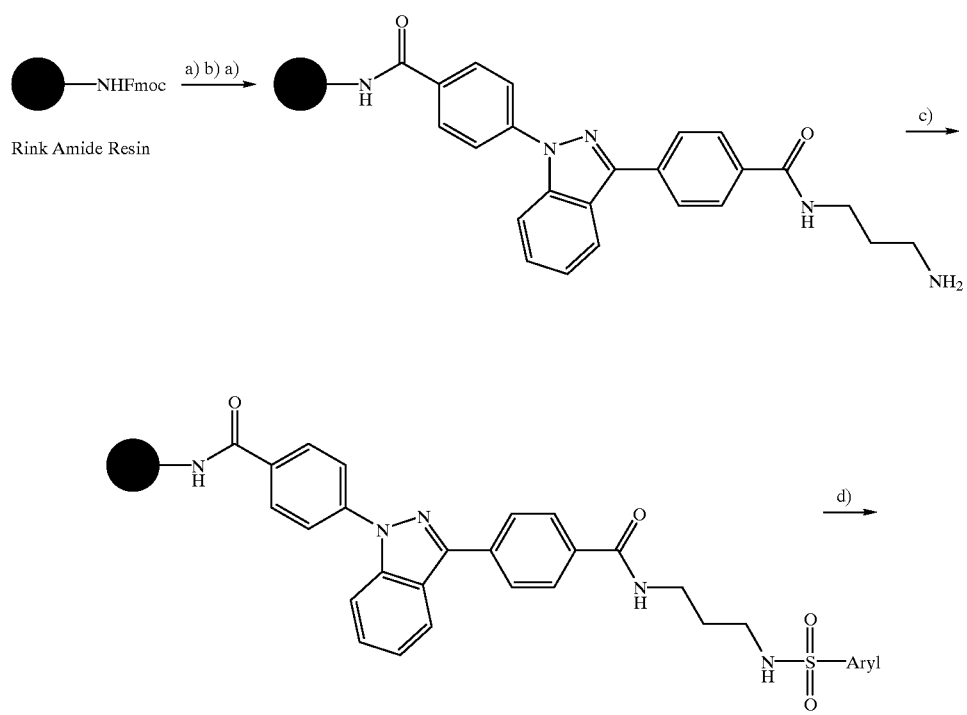
Scheme 6

-continued

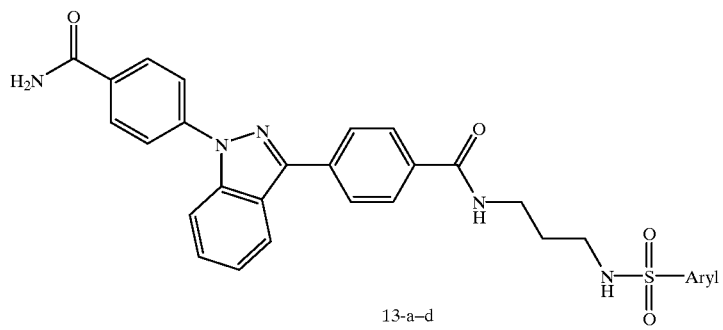

13-a–d

Conditions:
(a) DCM/piperidine.
(b) 6, DIC, HOBt, DMF, RT, 7 h.
(c) DCM/TEA, ArSO2Cl, RT, 3 h.
(d) DCM/TFA, RT, 20 min.

Rink amide resin (500 mg; 0.28 mmol) is shaken with piperidine (20%) in dichloromethane (10 mL) at room temperature for 1 h. The resin is washed with portions of dichloromethane, methanol and finally dichloromethane, until a sample of the latest filtrate shows no presence of cleaved protecting group. The resin is shaken in a solution prepared from 6 (0.56 mmol), 1-hydroxybenzotriazole (1.68 mmol), N,N'-diisopropyl carbodiimide (2.24 mmol) and dimethylformamide (35 mL) overnight at room temperature. The resin is washed thoroughly with several portions of dimethylformamide, then methanol, and finally dichloromethane. The washing continues until the latest filtrate is free of fluorescence. Solvents are evaporated under reduced pressure at room temperature. The Fmoc protecting group of resin bound 6 is removed as described above for deprotection of the Rink amide resin. The resin is dried for 30 min under reduced pressure. Portions of the resin (80 mg, each) are slightly stirred in dichloromethane (5 mL) containing triethylamine (10% v/v). Different arylsulfonylchlorides (a-d; 0.16 mmol, each) are added at room temperature. After 3 h the reagents are filtered off, and the resins are washed with several portions of dichloromethane, methanol, finally with dichloromethane. After drying in a desiccator under reduced pressure, each resin is treated with 3 mL of dichloromethane/trifluoroacetic acid (4/1) for cleavage of the products. The cleavage solutions are collected by filtration, and the resins are washed with three portions of dichloromethane (2 mL, each). Solvents are removed under reduced pressure in a desiccator containing sodium hydroxide. The purity of the products (13a–d) is analyzed by RP-HPLC, and the presence of the compounds 13a–d is verified by mass spectrometry:

| 13 | Aryl | Yield [%] HPLC [%] | MS (ESI) | 13 | Aryl | Yield [%] HPLC [%] | MS (ESI) |
|---|---|---|---|---|---|---|---|
| a | (4-methylphenyl) | 32 / 92 | 568 (MH)+ | c | (3-nitrophenyl) | 57 / 85 | 599 (MH)+ |
| b | (5-dimethylamino-naphthalenyl) | 57 / 85 | 647 (MH)+ | d | (4-methoxyphenyl) | 79 / 87 | 584 (MH)+ |

EXAMPLE 7B

4-[3-(4Carbamoyl-phenyl)-indazol-1-yl]-N-[2-(cyclopropylmethyl-carbamoyl)-ethyl]-benzamide (14) as illustrated in Scheme 7

Scheme 7

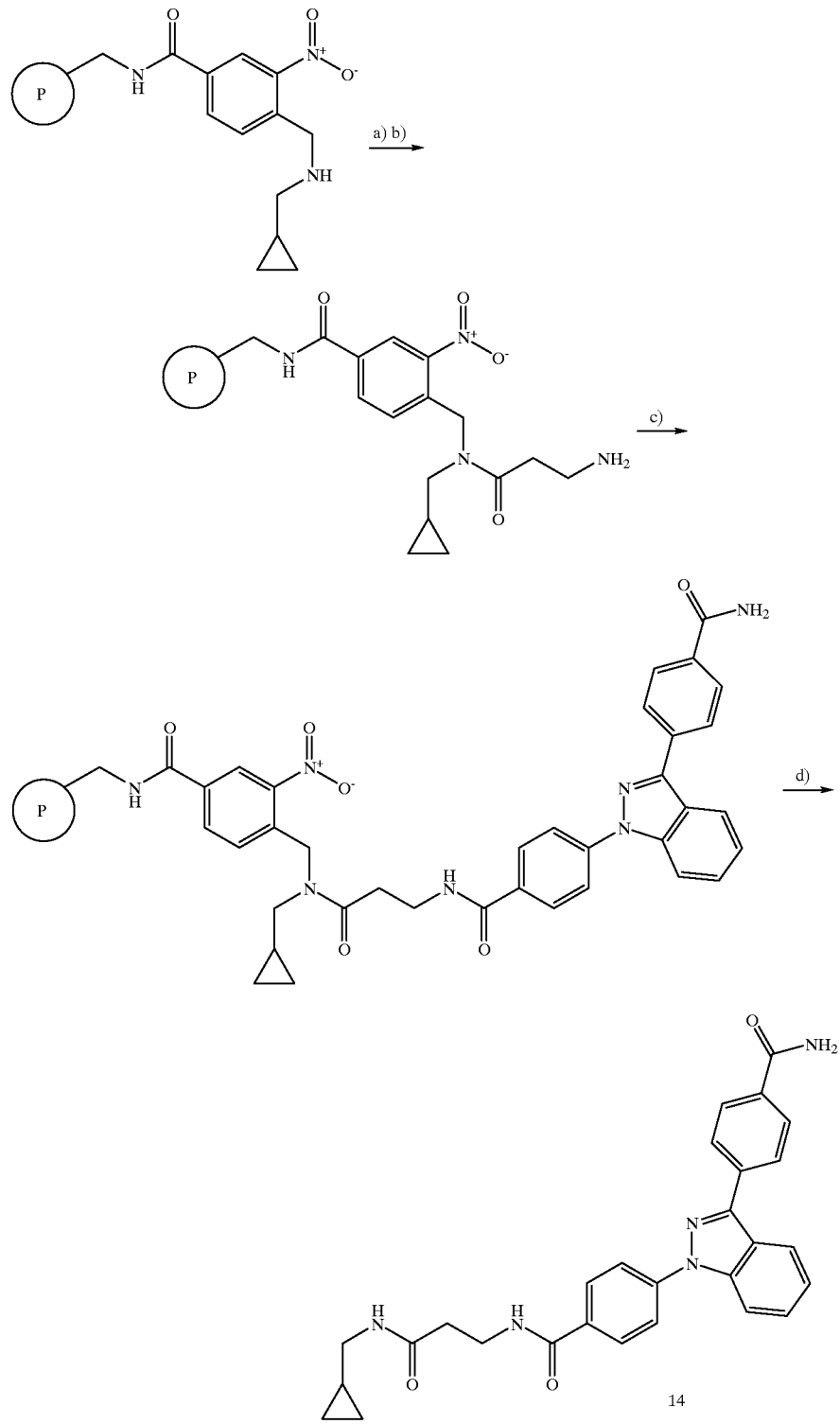

Aminoethyl-Tentagel resin (capacity: 0.29 mmol/g) is loaded with photolabile 4-bromomethyl-3-nitro benzoic acid linker by standard procedure and subsequently reacted with cyclopropylmethylamine as described in example 5B. To a solution of Fmoc-β-alanine (181 mg, 0.58 mmol) and 1-hydroxybenzotriazole (235 mg, 1.74 mmol) in DMF (5 mL) is added N,N'-diisopropylcarbodiimide (293 mg, 2.32 mmol). The solution is left for 1 h at room temperature. The cyclopropylmethylamine loaded resin (500 mg) is added and slight stirring is applied for 12 h. The resin is filtered off and washed with DMF, MeOH, and DCM. The resin is added to a solution (5 mL) of active ester of 4c prepared as described in example 5B. The reaction mixture is shaken at room temperature overnight. The reagents are removed by filtration. The resin is washed with several portions of DMF, MeOH, and finally with DCM. The resin is transferred into a glass vial and covered by DCM (5 mL). MeOH is added to achieve isodense solution. The vial is shaken under irradiation with an UV-lamp (366 nm) for 24 h. After this time the resin is removed by vacuum filtration and the solvents evaporated to dryness. The purity of the product (14) is analyzed by RP-HPLC, and the presence of the compound 14 is verified by mass spectrometry: m/e=482 (MH$^+$).

TABLE 1

| | | Absorption $\lambda_{max}$ | Emission $\lambda_{max}$ | Excitation $\lambda_{max}$ |
|---|---|---|---|---|
| 4a | | 328 nm $\epsilon$ = 22569 M$^{-1}$ cm$^{-1}$ | 396 nm (360–450 nm)* | 328 nm (300–340 nm)* |
| 4b | | 334 nm $\epsilon$ = 29152 M$^{-1}$ cm$^{-1}$ | 396 nm (360–500 nm) | 335 nm (300–360 nm) |
| 4c | | 332 nm $\epsilon$ = 30665 M$^{-1}$ cm$^{-1}$ | 393 nm (360–500 nm) | 334 nm (300–360 nm) |
| 4d | | 334 nm $\epsilon$ = 33114 M$^{-1}$ cm$^{-1}$ | 396 nm (360–500 nm) | 336 nm (300–360 nm) |
| 4e | | 335 nm $\epsilon$ = 34134 M$^{-1}$ cm$^{-1}$ | 398 nm (360–480 nm) | 337 nm (310–360 nm) |

TABLE 1-continued

| | | Absorption λ$_{max}$ | Emission λ$_{max}$ | Excitation λ$_{max}$ |
|---|---|---|---|---|
| 4f | [structure: 4-(3-(4-nitrophenyl)-1H-indazol-1-yl)benzoic acid] | 354 nm ε = 25482 M$^{-1}$ cm$^{-1}$ | 554 nm (470–670 nm) | 368 nm (320–400 nm) |
| 4g | [structure: 4-(3-(4-chlorophenyl)-6-chloro-1H-indazol-1-yl)benzoic acid] | 328 nm ε = 29157 M$^{-1}$ cm$^{-1}$ | 364 nm (350–450 nm) | 328 nm (310–350 nm) |
| 4h | [structure: 4-(3-(4-methoxyphenyl)-6-methoxy-1H-indazol-1-yl)benzoic acid] | 327 nm ε = 27650 M$^{-1}$ cm$^{-1}$ | 439 nm (370–600 nm) | 330 nm (300–350 nm) |
| 4i | [structure: 4-(1-(4-nitrophenyl)-1H-indazol-3-yl)benzoic acid] | 361 nm ε = 31261 M$^{-1}$ cm$^{-1}$ | 551 nm (470–670 nm) | 374 nm (320–420 nm) |
| 4j | [structure: 4-(3-(4-nitrophenyl)-6-methyl-1H-indazol-1-yl)benzoic acid] | 358 nm ε = 24967 M$^{-1}$ cm$^{-1}$ | 565 nm (490–700 nm) | 370 nm (340–420 nm) |

TABLE 1-continued

| | | Absorption $\lambda_{max}$ | Emission $\lambda_{max}$ | Excitation $\lambda_{max}$ |
|---|---|---|---|---|
| 4k | [Structure: 1-(4-carboxyphenyl)-3-(4-carboxyphenyl)-5-nitro-1H-indazole] | 328 nm $\epsilon = 22622$ $M^{-1}$ $cm^{-1}$ | 524 nm (450–620 nm) | 331 nm (320–360 nm) |
| 4l | [Structure: 1-(4-carboxyphenyl)-3-(4-carbamoylphenyl)-5-nitro-1H-indazole] | 326 nm $\epsilon = 17252$ $M^{-1}$ $cm^{-1}$ | 527 nm (450–620 nm) | 331 nm (310–360 nm) |

Solvent: acetonitrile/2% DMSO; range in parenthesis

TABLE 2
| | | Absorption $\lambda_{max}$ | Emission $\lambda_{max}$ | Excitation $\lambda_{max}$ |
|---|---|---|---|---|
| 8 | 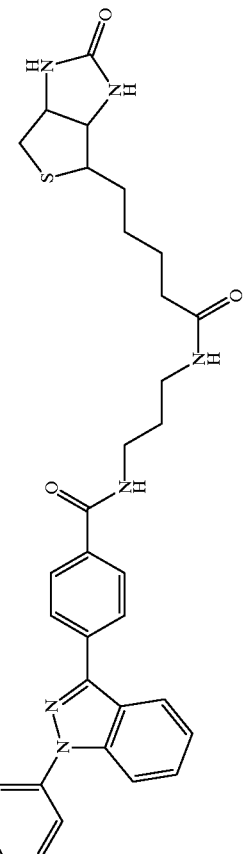 | 331 nm $\epsilon$ = 32158 M$^{-1}$ cm$^{-1}$ | 394 nm (360–480 nm) | 332 nm (310–360 nm) |
| 11 | 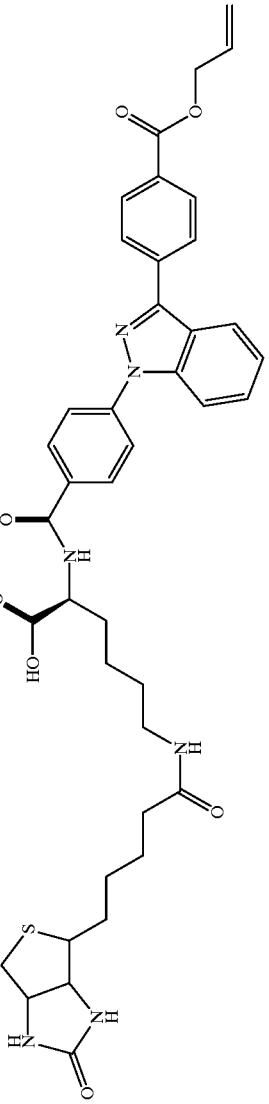 | 334 nm $\epsilon$ = 34349 M$^{-1}$ cm$^{-1}$ | 397 nm (370–480 nm) | 336 (310–360 nm) |
Solvent: acetonitrile/2% DMSO; range in parenthesis.

References

Literature related to synthesis of 1,3-diarylindazoles

Elderfield, R. C. in "Heterocyclic Compounds" (1957), ed. Elderfield, R. C., vol 5, John Wiley & Sons, Inc., New York, p.162.

Dalla Croce, Piero; La Rosa, Concetta. Synthesis (1984), 11, 982–3.

Yan, B.; Gstach, H. Tetrahedron Lett. (1996), 37(46), 8325–8.

Wang, Q.; Jochims, J..; Koehlbrandt, S.; Dahlenburg, L.; Al-Talib, M.; Hamed, A., Ismail, Abd El Hamid. Synthesis (1992), 7, 710-8.

Krishnan, R.; Lang, S. A., Jr.; Lin, Yang I; Wilkinson, R. G. J. Heterocycl. Chem. (1988), 25(2), 447–52.

Matsugo, Seiichi; Saito, Mitsuo; Kato, Yohko; Takamizawa, Akira. Chem. Pharm. Bull. (1984), 32(6), 2146–53.

Matsugo, Seiichi; Takamizawa, Akira. Synthesis (1983), 10, 852.

Theilacker, W.; Raabe, C. Tetrahedron Lett. (1966), 91–92.

Gladstone, W. A. F.; Norman, R. O. C. J. Chem. Soc. (1965), 3048–52.

Fries, K.; Fabel, K.; Eckhardt, H. Justus Liebigs Ann. Chem. (1942), 550, 31–49.

Borsche, W.; Scriba, W. Justus Liebigs Ann. Chem. (1939), 540, 83–98.

Huisgen, R.; Seidel, M.; Walibillich, G.; Knupfer, H. Tetrahedron (19.62), 17, 3–29.

Gladstone, W. A. F.; Norman, R. O. C. J. Chem. Soc. (1965), 5177–82.

Huisgen, R.; Knupfer, H.; Sustmann, R.; Walibillich, G.; Weberndörfer, V. Chem. Ber. (1967), 100, 1580–92.

Fries, K.; Tampke, H. Justus Liebigs Ann. Chem. (1927), 454, 303–24.

Pummerer, R.; Buchta, E.; Deimler, E. Chem. Ber. (1951), 84(7), 583–90.

Dennler, E. B.; Frasca, A. R. Tetrahedron (1966), 22, 3131–41.

Gladstone, W. A. F.; Harrison, M. J.; Norman, R. O. C. J. Chem. Soc. (1966), 1781.1

Literature for optical spectroscopy related to indazoles

Saha, Subit K.; Dogra, Sneh K. J. Photochem. Photobiol., A (1997), 110(3), 257–266.

Phaniraj, P.; Mishra, Ashok K.; Dogra, S. K. Indian J. Chem., Sect. A (1985), 24A(11), 913–17.

Mishra, A. K.; Swaminathan, M.; Dogra, S. K. J. Photochem. (1984), 26(1), 49–56.

Specificic literature for fluorescence and UV-spectroscopy used in the experimental parts Melhuish, W. H. (1961) J. Phys. Chem. 65, 229.

Demas, J. N., & Crosby, G. A. (1971) J. Phys. Chem. 75, 991–1024.

Chen, R. F. (1972) J. of Research of the International Bureau of Standards Vol. 76A No. 6, 593–606.

Lakowicz, J. R. (1983, pages 52–93, 112–153, 156–185) Principles of Fluorescence Spectroscopy, Plenum Press, New York and London.

Savage, M. D. et al., Avidin-Biotin Chemistry, Pierce Chemical Company, (1992).

Petrich, J. W., Chang, M. C., McDonald, D. B., Fleming, G. R., (1983) J. Am. Chem. Soc. 105, 3824–3832.

Szabo, A. G., Rayner, D. M. (1980) J. Am. Chem. Soc. 102, 554–563.

Pugliese, L., Coda, A., Malcovati, M., Bolognesi, M. (1993) J. Mol. Biol. 231, 698

Legends to Figures

(i) FIG. 1

(a) Absorption spectrum, of 25 $\mu$M 4e in THF and fluorescence excitation spectrum ( . . . ). The small red shift in the fluorescence excitation spectrum is caused by monochromator deviations between the UV and the fluorescence instrument.

(b) Fluorescence emission, 1 $\mu$M in THF, excitation at 342 nm.

(ii) FIGS. 2a and 2b (a) —(i) Excitation and emission spectra of AlDA-conjugates 11, 9, and 8, (in the graphical representation assigned as BLI, BPI, and IPB, respectively), and Avidin-Tryptophan, Avidin Lucifer Yellow and Avidin-BODIPY-FL, showing the overlap between tryptophan, BODIPY-FL and Lucifer Yellow emission and excitation, respectively.

Figure 3:
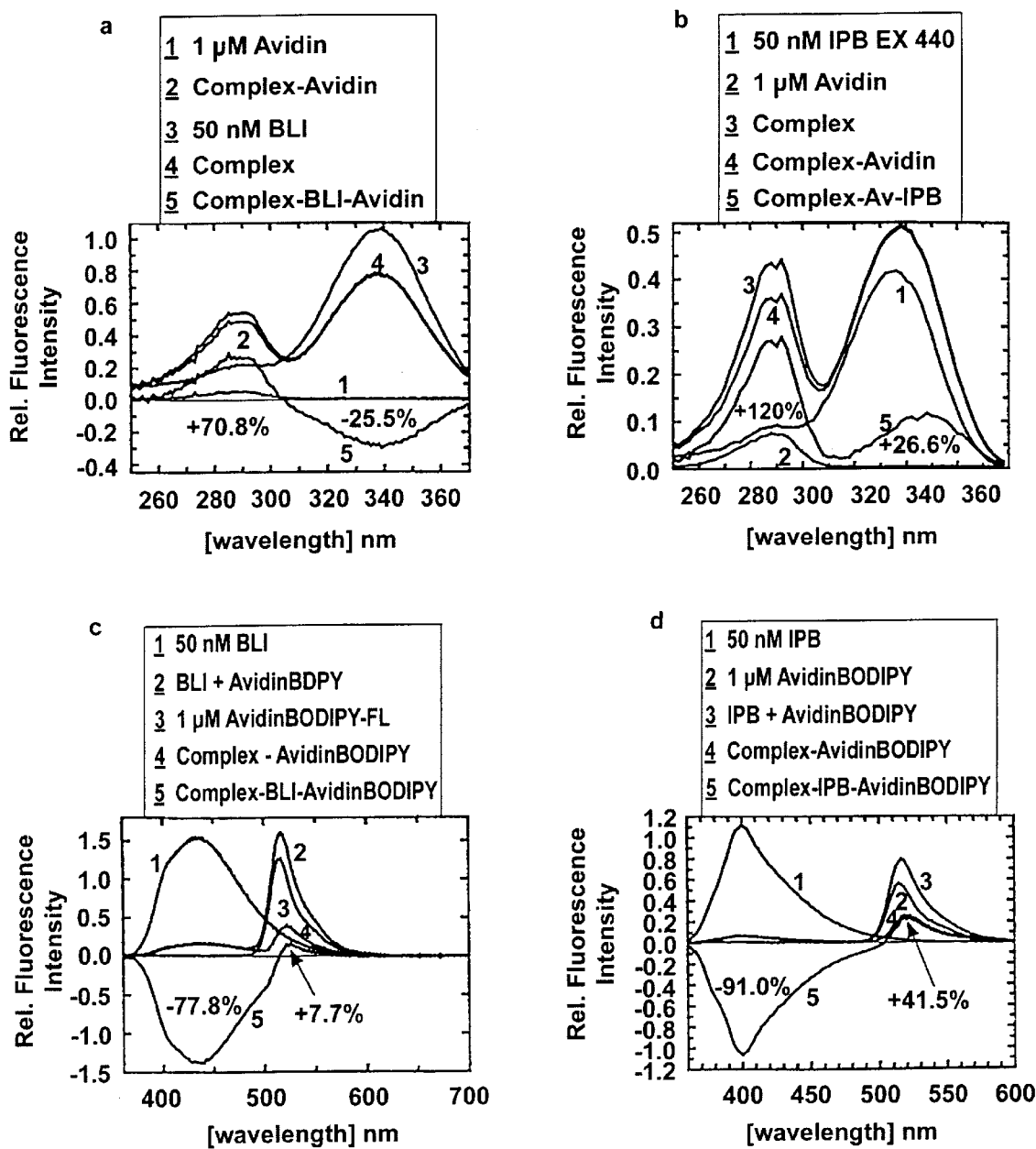

(iii) FIG. 3

Upper panel

Fluorescence resonance energy transfer and ground state quenching in the 11 (BLI) (a) and 8 (IPB) (b) tryptophan avidin complexes. The curves are assigned by numbers 1–5.

The difference spectra [|(11 or 8(free))+|(avidin(free))]-| (11- or 8-avidin Complex) are shown in curves 5.

The 11 fluorescence is quenched by about 25.5% by complexation in the avidin binding site. Approximately 62% of this total quenching effect is fluorescence resonance energy transfer. From 250 to 305 nm the enhancement of the tryptophan and tyrosine fluorescence intensity is 72% based on the sum of 11 and avidin. Linking the biotin to position 3 in the indazole molecule (from position 1 in 11) not only changes the fluorescence spectra, but also the tryptophan→indazole FRET characteristics: Indicated by 26% increase in indazole fluorescence emission (instead of quenching) an enhanced energy transfer to tryptophan (120%) is superimposed by a strong increase in indazole quantum yield in the avidin environment.

Lower panel

Fluorescence resonance energy transfer and ground state quenching in the 11 (c) and 8 (d)BODIPY-FL avidin complexes.The curves are assigned by numbers 1–5. With both molecular geometries, the indazole tracer linked via position 1 (11) and position 3(8), binding of BODIPY-FL labelled avidin causes a 70-90% quenching of the indazole emission. This reduction in signal intensity can be caused by ground state quenching of the indazole or FRET to the BODIPY labels on avidin with concurrent non-radiative depopulation of the excited state. Although the overlap integral between the indazole emission and the BODIPY-FL absorption spectrum is smaller for 8 than for 11, more sensitization of acceptor fluorescence occurs in the 8-avidin BODIPY complex resulting in 48% fluoresence energy transfer and 93.5% indazole donor quenching.

This effect can be caused by a higher donor quantum yield or a prefered relative orientation of the donor emission and acceptor absoprtion dipoles in 8.

What is claimed is:

1. Compounds represented by formula (I)

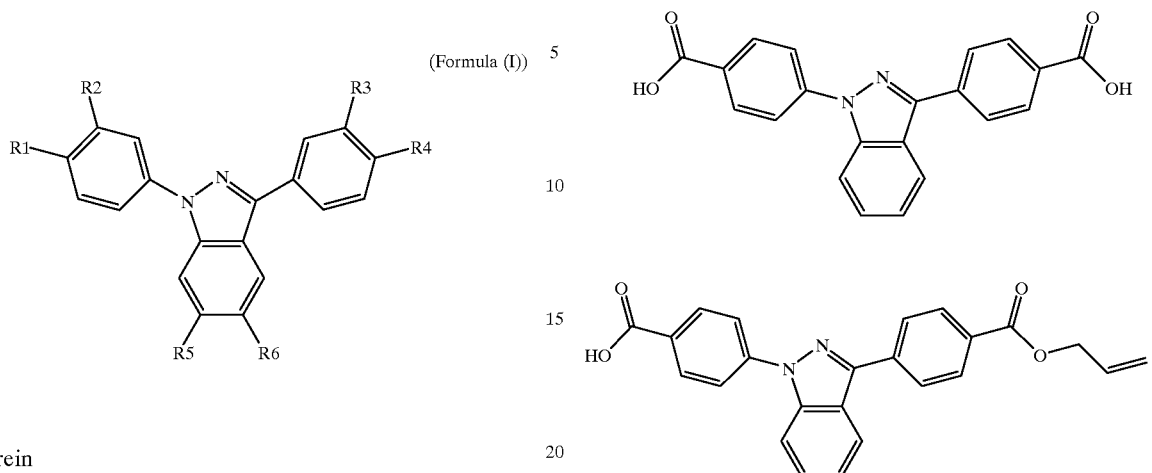

(Formula (I))

wherein one of the radicals $R^1$ or $R^2$ and one of the radicals $R^3$ or $R^4$ is hydrogen and the other is independently —COOH, —COOR$^7$, —CONH$_2$, —CONH(CH$_2$),OH, wherein n=2–8, —CONR$^8$R$^9$, —CH$_2$OH, —CH$_2$NH$_2$, —NO$_2$, NR$^{10}$OR$^{11}$, NHCOR$^{12}$, Cl, Br, F, —CF$_3$, —N=C=O, N=C=S, —SO$_3$H, —SO$_2$NH(CH$_2$)$_n$NH$_2$, (C$_1$–C$_4$) alkyl, (C$_1$–C$_{16}$)-alkyl substituted at the terminal carbon with —COOH, —COOR$^7$, —CONH$_2$, —CONR$^8$R$^9$, —CONH(CH$_2$)$_n$OH, wherein n=2–8, —CH$_2$OH, —CH$_2$NH$_2$, —N=C=O, N=C=S, —SO$_3$H, —SO$_2$NH(CH$_2$)$_n$NH$_2$, —CONH(CH$_2$)$_n$NH$_2$ wherein n=2–8, and the NH$_2$-group could also be substituted by (C$_1$–C$_4$) alkyl or a commonly used amino protecting group, and one of the radicals $R^5$ or $R^6$ is hydrogen and the other is hydrogen, halogen, —NO$_2$, NR$^{10}$OR$^{11}$, NHCOR$^{12}$, (C$_1$–C$_4$) alkyl, (C$_1$–C$_{16}$)-alkyl substituted at the terminal carbon with —COOH, —COOR$^7$, —CONH$_2$, —CONR$^8$R$^9$, —CONH(CH$_2$)$_n$OH, wherein n=2–8, —CH$_2$OH, —CH$_2$NH$_2$, —N=C=O, N=C=S, —SO$_3$H, —SO$_2$NH(CH$_2$)$_n$NH$_2$, —CONH(CH$_2$)$_n$NH$_2$ wherein n=2–8, and the NH$_2$-group could also be substituted by (C$_1$–C$_4$) alkyl or a commonly used amino protecting group, with the proviso that only one of $R^1$–$R^6$ is nitro, $R^7$ is a commonly used carboxyl protecting or carboxyl activating group, $R^8$ or $R^9$ is hydrogen and the other is lower alkyl (C$_1$–C$_4$), phenyl, benzyl, or $R^8$ and $R^9$ are part of a 5 or 6 membered ring, $R^{10}$ and $R^{11}$ are independently hydrogen or (C$_1$–C$_4$)alkyl, and $R^{12}$ is (C$_1$–C$_{10}$)alkyl or phenyl, which both can be substituted by (C$_1$–C$_4$) alkyl, protected amino group or halogen.

2. Compounds according to claim 1 represented by the following structures:

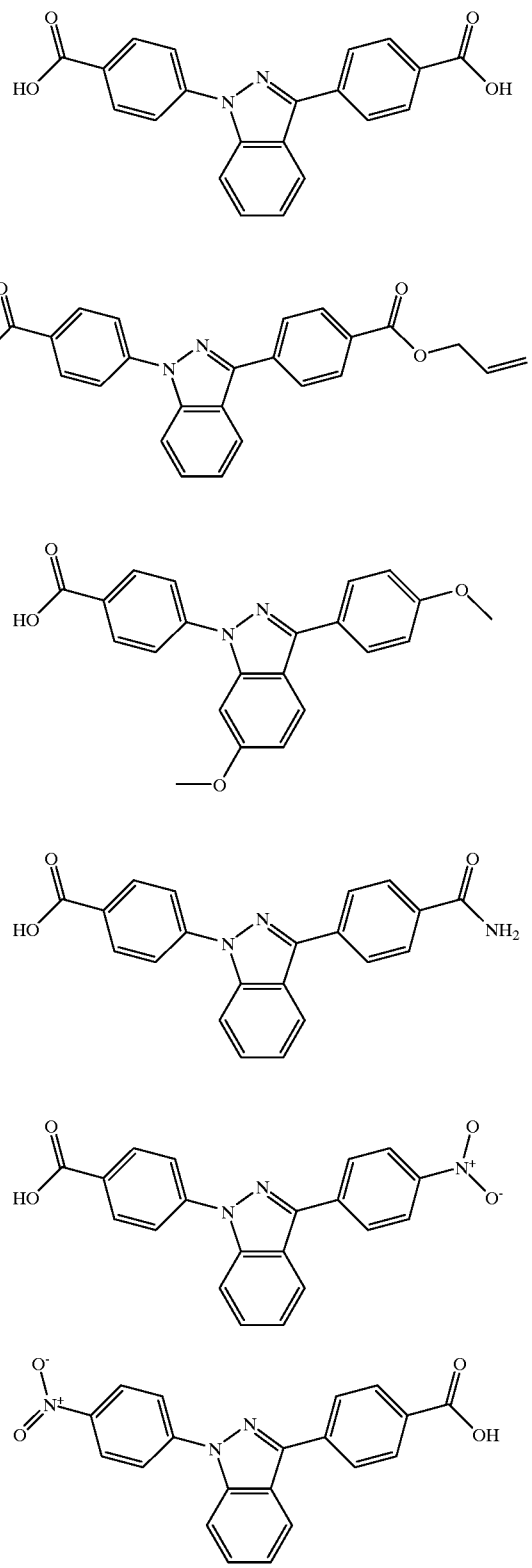

-continued
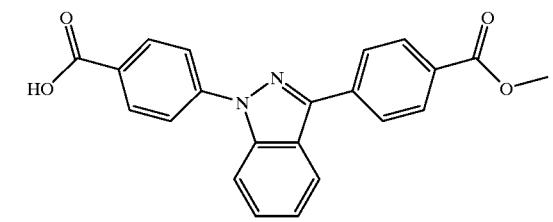
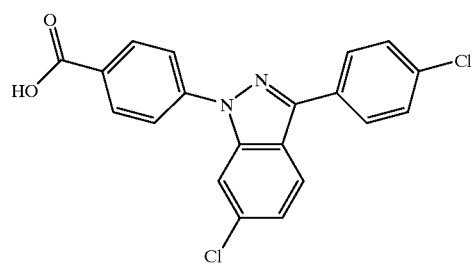
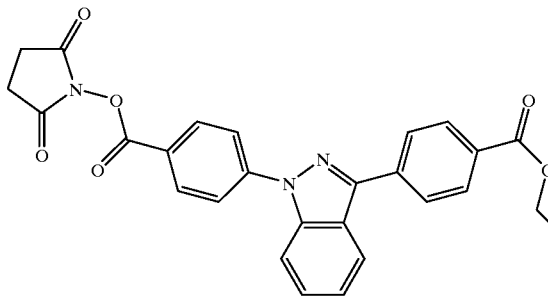
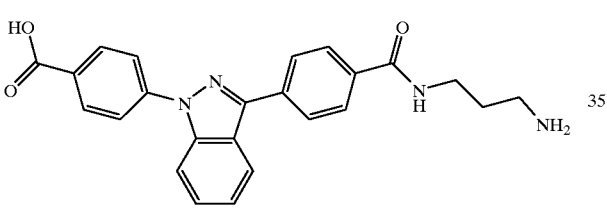
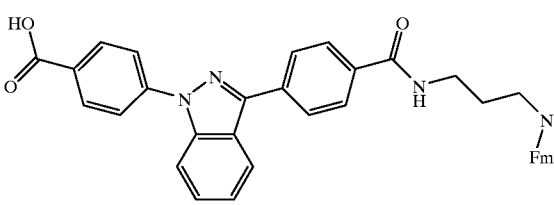
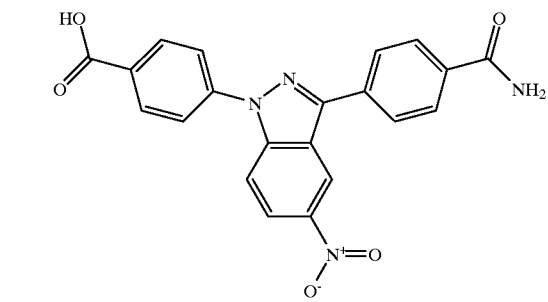
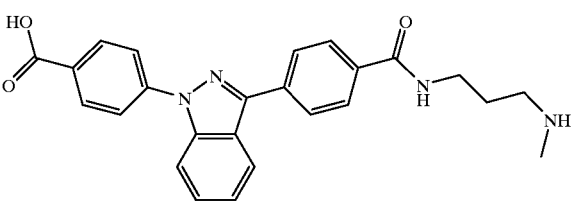
-continued
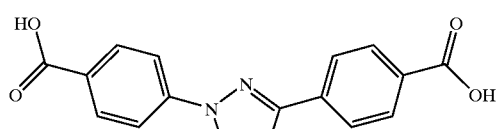
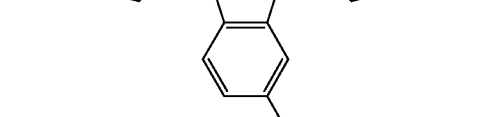
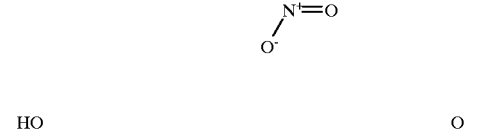
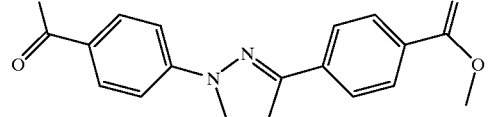
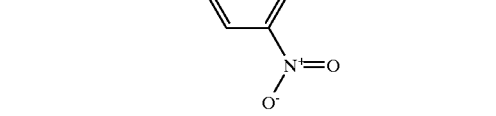
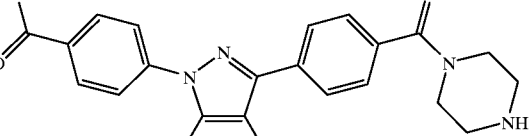
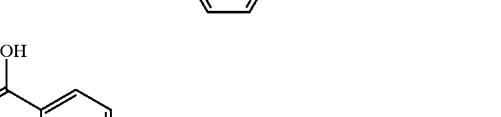
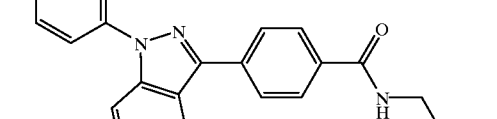
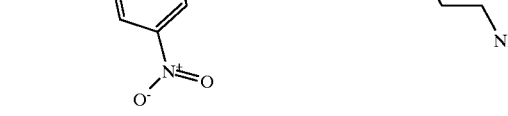
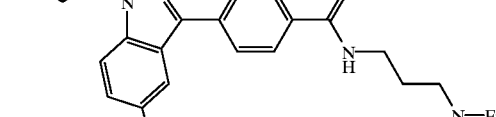
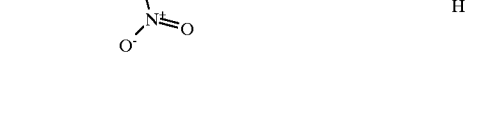

73
-continued
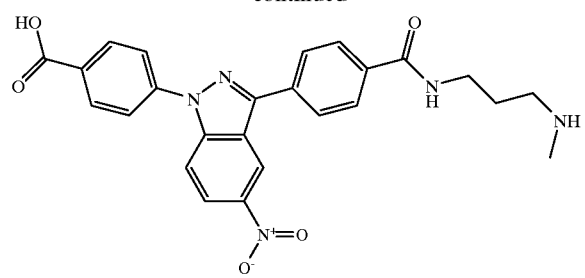
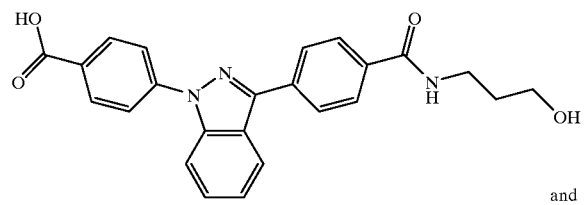
and
74
-continued
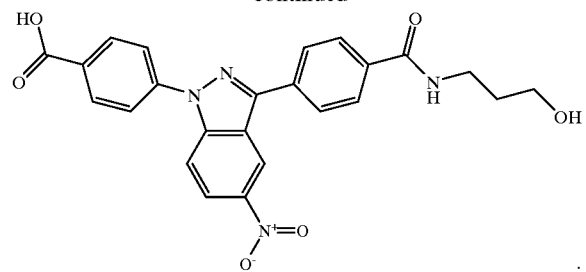
.
3. A compound of claim 1 wherein the protecting group is tert-butyloxycarbonyl, 9-fluorenylmethoxycarbonyl, phthalimido, trifluoroacetamido, methoxycarbonyl, ethoxycarbonyl, benzyloxycarbonyl, allyloxycarbonyl, 2,2,2-trichloroethoxycarbonyl, or 2-(trimethylsilyl)ethoxycarbonyl.
* * * * *

UNITED STATES PATENT AND TRADEMARK OFFICE
CERTIFICATE OF CORRECTION

PATENT NO. : 6,207,831 B1
DATED : March 27, 2001
INVENTOR(S) : Auer et al.

Page 1 of 1

It is certified that error appears in the above-identified patent and that said Letters Patent is hereby corrected as shown below:

<u>Column 69,</u>
Line 24, should read:
-- -COOH, -COOR$^7$, -CONH$_2$, -CONH(CH$_2$)$_n$OH, --
Line 39, should read:
-- is hydrogen, halogen, -NO$_2$, NR$^{10}$R$^{11}$, NHCOR$^{12}$, --

Signed and Sealed this

Thirty-first Day of December, 2002

JAMES E. ROGAN
*Director of the United States Patent and Trademark Office*